US010753933B2

(12) United States Patent
Singhal et al.

(10) Patent No.: US 10,753,933 B2
(45) Date of Patent: *Aug. 25, 2020

(54) METHODS FOR ASSAYING CELLULAR BINDING INTERACTIONS

(71) Applicant: The University of British Columbia, Vancouver (CA)

(72) Inventors: Anupam Singhal, Mississauga (CA); Carl L. G. Hansen, Vancouver (CA); John W. Schrader, Vancouver (CA); Charles A. Haynes, Vancouver (CA); Daniel J. Da Costa, Pitt Meadows (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/815,887

(22) Filed: Mar. 11, 2020

(65) Prior Publication Data

US 2020/0225225 A1    Jul. 16, 2020

Related U.S. Application Data

(63) Continuation of application No. 16/746,540, filed on Jan. 17, 2020, which is a continuation of application
(Continued)

(51) Int. Cl.
*B01L 3/00* (2006.01)
*G01N 33/569* (2006.01)
(Continued)

(52) U.S. Cl.
CPC .. *G01N 33/56966* (2013.01); *B01L 3/502738* (2013.01); *B01L 3/502761* (2013.01);
(Continued)

(58) Field of Classification Search
None
See application file for complete search history.

(56) References Cited

U.S. PATENT DOCUMENTS

| 5,874,085 A | 2/1999 | Mond et al. |
| 6,007,690 A | 12/1999 | Nelson et al. |

(Continued)

FOREIGN PATENT DOCUMENTS

| WO | 2003085379 A3 | 12/2003 |
| WO | 2005069980 A2 | 8/2005 |

(Continued)

OTHER PUBLICATIONS

Jerne (1984) "The generative grammar of the immune system" EMBO J. 4(4):847-852.
(Continued)

*Primary Examiner* — Rebecca M Giere
(74) *Attorney, Agent, or Firm* — Potomac Law Group PLLC

(57) ABSTRACT

There are provided methods, and devices for assaying for a binding interaction between a protein, such as a monoclonal antibody, produced by a cell, and a biomolecule. The method may include retaining the cell within a chamber having an aperture; exposing the protein produced by the cell to a capture substrate, wherein the capture substrate is in fluid communication with the protein produced by the cell and wherein the capture substrate is operable to bind the protein produced by the cell; flowing a fluid volume comprising the biomolecule through the chamber via said aperture, wherein the fluid volume is in fluid communication with the capture substrate; and determining a binding interaction between the protein produced by the cell and the biomolecule.

30 Claims, 29 Drawing Sheets

Related U.S. Application Data

No. 16/579,561, filed on Sep. 23, 2019, now Pat. No. 10,578,618, which is a continuation of application No. 16/290,751, filed on Mar. 1, 2019, now Pat. No. 10,466,241, which is a continuation of application No. 16/129,555, filed on Sep. 12, 2018, now Pat. No. 10,274,494, which is a continuation of application No. 14/879,791, filed on Oct. 9, 2015, now Pat. No. 10,107,812, which is a continuation of application No. 13/184,363, filed on Jul. 15, 2011, now Pat. No. 9,188,593.

(60) Provisional application No. 61/365,237, filed on Jul. 16, 2010.

(51) Int. Cl.
G01N 33/68 (2006.01)
G01N 33/58 (2006.01)
G01N 33/577 (2006.01)

(52) U.S. Cl.
CPC ......... *G01N 33/577* (2013.01); *G01N 33/582* (2013.01); *G01N 33/6854* (2013.01); *B01L 2200/0668* (2013.01); *B01L 2300/0681* (2013.01); *B01L 2300/0861* (2013.01); *B01L 2300/0864* (2013.01); *B01L 2300/0867* (2013.01); *B01L 2400/0481* (2013.01)

(56) References Cited

U.S. PATENT DOCUMENTS

| | | |
|---|---|---|
| 7,143,785 B2 | 12/2006 | Maerkl et al. |
| 8,124,015 B2 | 2/2012 | Diercks et al. |
| 9,188,593 B2 | 11/2015 | Singhal et al. |
| 10,107,812 B2 | 10/2018 | Singhal et al. |
| 10,274,494 B2 | 4/2019 | Singhal et al. |
| 2002/0164656 A1 | 11/2002 | Hoeffler et al. |
| 2009/0068170 A1 | 3/2009 | Weitz et al. |
| 2010/0086919 A1 | 4/2010 | McKeon |
| 2011/0262906 A1 | 10/2011 | Dimov et al. |
| 2011/0294678 A1 | 12/2011 | Jin et al. |
| 2013/0130301 A1 | 5/2013 | Yoon et al. |

FOREIGN PATENT DOCUMENTS

| | | |
|---|---|---|
| WO | 2009012340 A2 | 1/2009 |
| WO | 2010046775 A2 | 4/2010 |
| WO | 2012162779 A1 | 12/2012 |

OTHER PUBLICATIONS

Abdiche et al. (2008) "Determining kinetics and affinities of protein interactions using a parallel real-time label-free biosensor, the Octet" Analytical Biochemistry 377(2):209-217.
Babcook et al. (1996) "A novel strategy for generating monoclonal antibodies from single, isolated lymphocytes producing antibodies of defined specificities" Proc. Natl. Acad. Sci. USA 93(15):7843-7848.
Bates & Quake (2009) "Highly parallel measurements of interaction kinetic constants with a microfabricated pptomechanical device" Appl. Phys. Lett. 95(7):73705.
Batista & Neuberger (1998) "Affinity dependence of the B cell response to antigen: a threshold, a ceiling, and the importance of off-rate" Immunity 8(6):751-759.
Biacore Life Sciences—Biacore 3000 System Information. (2012). Website: http://www.biacore.com/lifesciences/products/systems_overview/3000/system_information/index.html.
Biacore Life Sciences—Single-Cycle Kinetics. (2012). Website: https://www.biacore.com/lifesciences/technology/introduction/data_interaction/SCK/index.html.
Bornhop et al. (2007) "Free-solution, label-free molecular interactions studied by back-scattering interferometry" Science 317(5845):1732-1736.
Cai et al. (2006) "Stochastic protein expression in individual cells at the single molecule leve" Nature 440 (7082)358-362.
Dlugosz et al. (2009) "pH-dependent association of proteins. The test case of monoclonal antibody HyHEL-5 and its antigen hen egg white lysozyme" The Journal of Physical Chemistry 113(47):15662-15669.
England et al. (1999) "Functional characterization of the somatic hypermutation process leading to antibody D1.3, a high affinity antibody directed against lysozyme" J. Immunol. 162(4):2129-2136.
Hansen et al. (2002) "A robust and scalable microfluidic metering method that allows protein crystal growth by free interface diffusion" Proc. Natl. Acad. Sci. USA 99(26):16531-16536.
Hansen et al. (2004) "Systematic investigation of protein phase behavior with a microfluidic formulator" Proc. Natl. Acad. Sci. USA 101(40):14431-14436.
He & Niemeyer (2003) "A novel correlation for protein diffusion coefficients based on molecular weight and radius of gyration" Biotechnol. Prog. 19(2):544-548.
Homola et al. (1999) "Surface plasmon resonance sensors: review" Sensors and Actuators B: Chemical 54:3-15.
Huang et al. (2007) "Counting low-copy number proteins in a single cell" Science 315(5808):81-84.
Ito et al. (1995) "Mutations in the complementarity-determining regions do not cause differences in free energy during the process of formation of the activated complex between an antibody and the corresponding protein antigen" J. Mol. Biol. 248(4):729-732.
Jin et al. (2009) "A rapid and efficient single-cell manipulation method for screening antigen-specific antibody-secreting cells from human peripheral blood" Nat. Med.15(9):1088-1092.
Karpas et al. (2001) "A human myeloma cell line suitable for the generation of human monoclonal antibodies" Proc. Natl. Acad. Sci. USA 98(4):1799-1804.
Kohler & Milstein (1975) "Continuous cultures of fused cells secreting antibody of predefined specificity" Nature 256(5517):495-497.
Lanzavecchia et al. (2007) "Human monoclonal antibodies by immortalization of memory B cells" Current Opinion in Biotechnology 18(6):523-528.
Lecault et al. (2011) "High-Throughput Analysis of Single Hematopoietic Stem Cell Proliferation in Microfluidic Cell Culture Arrays" Nat Methods 8(7):581-586.
Lee et al. (2009) "High-sensitivity microfluidic calorimeters for biological and chemical applications" Proc. Natl. Acad. Sci. USA 106(36):15225-15230.
Maerkl & Quake (2007) "A systems approach to measuring the binding energy landscapes of transcription factors" Science 315(5809):233-237.
Marcus et al. (2006) "Microfluidic single-cell mRNA isolation and analysis" Anal. Chem. 78(9):3084-3089.
Mcdonald et al. (2000) "Fabrication of microfluidic systems in poly(dimethylsiloxane)" Electrophoresis 21: 27-40.
Mckinney et al. (1995) "Optimizing antibody production in batch hybridoma cell culture" J.Biotechnol. 40(1):31-48.
Pasqualini & Arap (2004) "Hybridoma-free generation of monoclonal antibodies" Proc. Natl. Acad. Sci. USA 101 (1):257-259.
Poulson et al. (2007) "Kinetic, affinity, and diversity limits of human polyclonal antibody responses against tetanus oxoid" J. Immunol. 179(6):3841-3850.
Raschke et al. (2003) "Biomolecular Recognition Based on Single Gold Nanoparticle Light Scattering" Nano Letters 3(7):935-938.
Sonnichsen et al. (2000) "Spectroscopy of single metallic nanoparticles using total internal reflection microscopy" App. Phys. Letters 77(19): 2949-2951.
Spieker-Polet et al. (1995) "Rabbit monoclonal antibodies: generating a fusion partner to produce rabbit-rabbit hybridomas" Proc. Natl. Acad. Sci. USA 92(20):9348-9352.
Squires & Quake (2005) "Microfluidics: Fluid physics at the nanoliter scale" Reviews of Modern Physics 77 (3):977-1026.

(56) References Cited

OTHER PUBLICATIONS

Story et al. (2008) "Profiling antibody responses by multiparametric analysis of primary B cells" Proc. Natl. Acad. Sci. U.S.A. 105(46):17902-17907.
Thorsen et al. (2002) "Microfluidic large-scale integration" Science 298(5593):580-584.
Tiller et al. (2009) "Cloning and expression of murine Ig genes from single B cells" J. Immunol. Methods 350 (1-2):183-193.
Traggiai et al. (2004) "An efficient method to make human monoclonal antibodies from memory B cells: potent neutralization of SARS coronavirus" Nat Med 10(8):871-875.
Tyn & Gusek (1990) "Prediction of diffusion coefficients of proteins" Biotechnol. Bioeng. 35(4):327-338.
Jeno et al. (2010) "Simple dark-field microscopy with nanometer spatial precision and microsecond temporal resolution" Biophysical J. 98(9):2014-2023.
Unger et al. (2000) "Monolithic microfabricated valves and pumps by multilayer soft lithography" Science 288 (5463)113-116.
Wang et al. (2005) "Label-free detection of small-molecule-protein interactions by using nanowire nanosensors" Proc. Natl. Acad. Sci. USA 102(9):3208-3212.
Xavier & Willson (1998) "Association and dissociation kinetics of anti-hen egg lysozyme monoclonal antibodies HyHEL-5 and HyHEL-10" Biophys. J. 74(4):2036-2045.

(1)

(2)

(3)

(4)

(5)

(6)

(7)

FIG. 12A
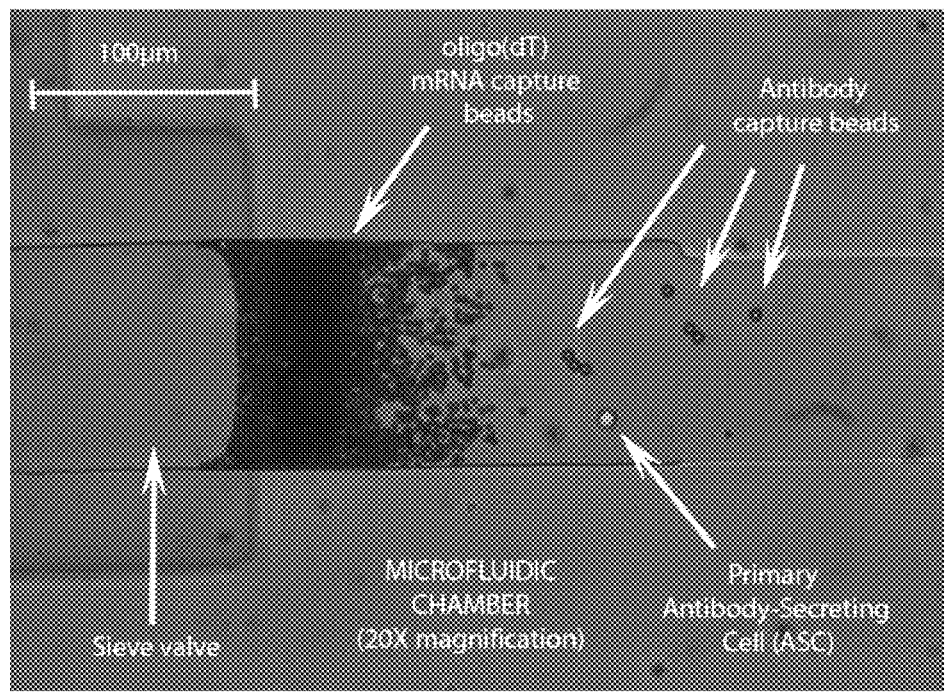
FIG. 12B
FIG. 12C
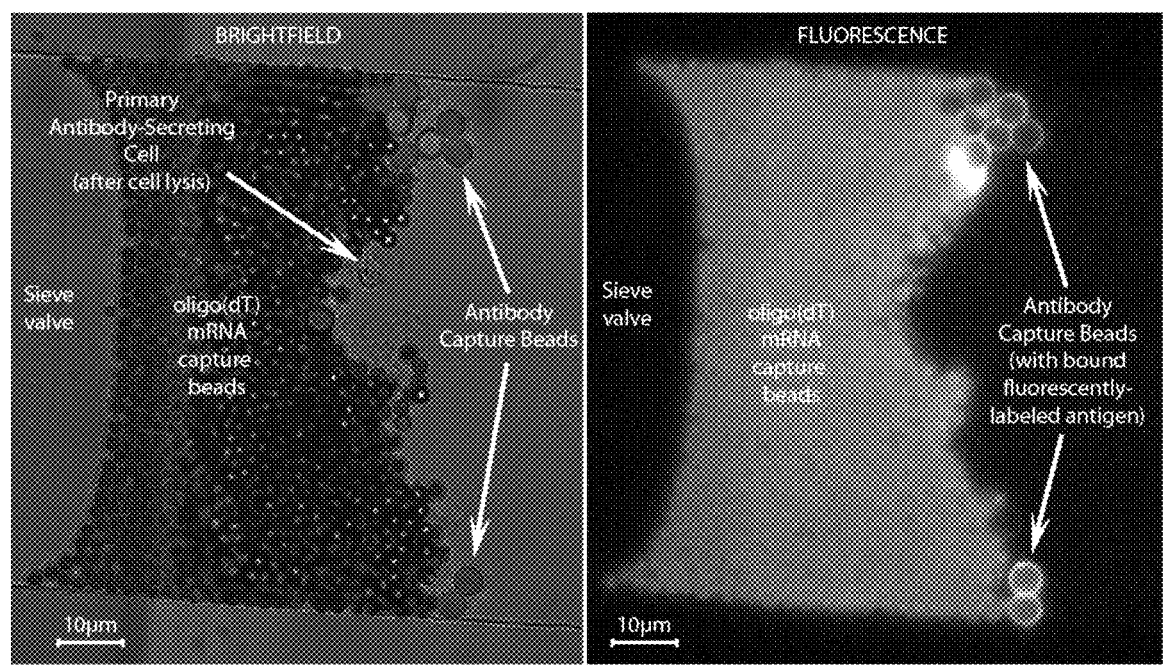

(1)

(2)

(3)

(4)

(5)

(6)

(7)

(8)

(9)

(10)

METHODS FOR ASSAYING CELLULAR BINDING INTERACTIONS

CROSS REFERENCE TO RELATED APPLICATIONS

This application is a continuation of U.S. patent application Ser. No. 16/746,540, filed Jan. 17, 2020, which is a continuation of U.S. patent application Ser. No. 16/579,561, filed Sep. 23, 2019, now U.S. Pat. No. 10,578,618, which is a continuation of U.S. patent application Ser. No. 16/290,751, filed Mar. 1, 2019, now U.S. Pat. No. 10,466,241, which is a continuation of U.S. patent application Ser. No. 16/129,555, filed Sep. 12, 2018, now U.S. Pat. No. 10,274,494, which is a continuation of U.S. patent application Ser. No. 14/879,791, filed Oct. 9, 2015, now U.S. Pat. No. 10,107,812, which is a continuation of U.S. patent application Ser. No. 13/184,363, filed Jul. 15, 2011, now U.S. Pat. No. 9,188,593, which claims the benefit of U.S. Provisional Patent Application Ser. No. 61/365,237 entitled "METHODS FOR ASSAYING CELLULAR BINDING INTERACTIONS" filed on Jul. 16, 2010, the disclosure of each of which is incorporated herein by reference in its entirety.

FIELD OF INVENTION

This invention relates to the field of microfluidics and protein binding, more specifically, binding interaction between biomolecules.

BACKGROUND

Antibodies are defense proteins produced by the vertebrate adaptive immune system for the purposes of binding and targeting for clearance of a diverse range of bacteria, viruses, and other foreign molecules (collectively referred to as antigens) (see, for e.g., Abbas et al. (1997), *Cellular and Molecular Immunology*, 3rd Ed., Chapter 3, pp. 37-65). As a result of their ability to bind target antigens selectively and with high affinity, antibodies are useful tools for protein purification, cell sorting, diagnostics, and therapeutics.

Conventional antibody production has involved the immunization of animals (i.e., mice) with a target antigen, such as a virus, bacteria, foreign protein, or other molecule. The immunized mice produce on the order of $10^4$-$10^5$ antibody secreting cells (ASCs), each with the capacity to produce a unique (monoclonal) antibody specific to the target antigen (see, for e.g., Poulson et al. (1997), *J. Immunol.* 179: 3841-3850; and Babcock et al. (1996), *Proc. Natl. Acad. Sci. USA* 93: 7843-7848).

The ASCs are then harvested from the immunized animals and screened in order to select which cells are producing antibodies of desired affinity and selectivity to the target antigen. Since single ASCs do not produce antibodies in sufficiently large quantities for binding affinity measurements, each ASC is clonally expanded. Primary ASCs do not grow efficiently in laboratory tissue cultures; thus, clonal expansion may be achieved by fusing ASCs to murine myeloma (cancer) cells to produce immortalized, antibody-secreting (hybridoma) cells (see, for e.g., Kohler, G. and Milstein, C. (1975), *Nature* 256: 495-497). Using this method, expansion of each successfully created hybridoma then produces a monoclonal antibody in sufficiently high concentrations to measure its affinity and selectivity to a target antigen.

It has been recognized that a limitation of hybridoma technology is the low efficiency of the fusion process. For example, whereas an immune response may produce on the order of $10^4$-$10^5$ antibody secreting cells, a typical fusion will yield less than 100 viable hybridomas. (see, for e.g., Kohler, G. and Milstein, C. (1975), *Nature* 256: 495-497; Karpas et al. (2001), *Proc. Natl. Acad. Sci. USA* 98: 1799-1804; and Spieker-Polet et al. (1995), *Proc. Natl. Acad. Sci. USA* 92: 9348-9352). Therefore, fusions from hundreds to thousands of animals are required to fully sample the diversity of antibodies produced in an immune response, making the hybridoma approach both time-consuming and expensive. Attempts to circumvent hybridoma generation by immortalizing antibody-producing cells using viral transformations have resulted in modest gains in the efficiency of ASC immortalization. However, these approaches still require costly and time-consuming clonal expansion in order to produce sufficient quantities of monoclonal antibodies to screen for affinity and selectivity to target antigens (see for e.g., Pasqualini, R. and Arap, W. (2004), *Proc. Natl. Acad. Sci. USA* 101: 257-259; Lanzavecchia et al. (2007), *Current Opinion in Biotechnology* 18: 523-528; and Traggiai et al. (2004), *Nat Med* 10: 871-875).

Devices have been developed to estimate the equilibrium dissociation constants of antibodies secreted from single antibody-secreting cells (Story, C. M. et al. *Proc. Natl. Acad. Sci. U.S.A.* (2008) 105(46):17902-17907; and Jin, A. et al. *Nat. Med.* (2009) 15(9):1088-1092), but do not measure antibody-antigen binding kinetics using antibodies secreted from single cells.

SUMMARY

In a first embodiment, there is provided a method of assaying for a binding interaction between a protein produced by a cell and a biomolecule: (a) retaining the cell within a chamber having an inlet and an outlet; (b) exposing the protein produced by the cell to a capture substrate, wherein the capture substrate is in fluid communication with the protein produced by the cell and wherein the capture substrate is operable to bind the protein produced by the cell; (c) flowing a first fluid volume comprising the biomolecule through the inlet into the chamber and out the outlet, wherein the first fluid volume is in fluid communication with the capture substrate; and (d) determining binding interactions between the protein produced by a cell and the biomolecule.

The cell may be an antibody producing cell (APC), the protein produced by the cell is an antibody and the biomolecule is an antigen. The cell may be a single cell. The biomolecule may be a fluorescently labeled antigen. The determining binding interactions may be a measure of antigen-antibody binding kinetics. The determining the antigen-antibody binding kinetics may include fluorescence imaging of antigen-antibody binding. The determining the binding interactions may be by one or more of the following techniques: surface plasmon resonance (SPR) spectroscopy, fluorescence anisotropy, interferometry, or fluorescence resonance energy transfer (FRET). The determining of the binding interaction may be by a nanocalorimeter or a nanowire nanosensor. The measure of antigen-antibody binding kinetics may be the $K_{on}$ rate. The measure of antigen-antibody binding kinetics may be the $K_{off}$ rate. The measure of antigen-antibody binding kinetics may be the both the $K_{on}$ rate and the $K_{off}$ rate. The protein produced by the cell may be an antibody. The antibody may be a monoclonal antibody. The protein produced by the cell may be an antigen. The biomolecule may be an antigen. The biomolecule may be selected from one of the following: an antibody, a whole cell, a cell fragment, a bacterium, a virus, a viral fragment, and a protein. The protein produced by the cell may not be secreted by the cell, and the method may further include a step of cell lysis prior to exposing the protein produced by the cell to the capture substrate. The protein produced by the cell may not be secreted by the cell, and the method may further include a step of cell lysis after exposing the protein produced by the cell to the capture substrate. The capture substrate may be a removable capture substrate. The removable capture substrate may be an anti-Ig bead. The removable capture substrate may be an anti-Ig bead and/or oligo (dT) bead. The removable capture substrate may include a capture substrate capable of capturing both nucleic acids and antibodies. The removable capture substrate may include a capture substrate capable of capturing nucleic acids and a capture substrate capable of capturing antibodies. The removable capture substrate may include a capture substrate capable of capturing nucleic acids. The binding of the antibodies may be further tested by viral inactivation. The binding of the antibodies may be further tested by bacterial inactivation. The binding of the antibodies may be further tested by cell inactivation. The method may further include adding the cell to a reverse transcription polymerase chain reaction (RT-PCR) reaction to amplify the heavy and light chain genes. The amplification may be performed in a number of ways. For example, 1) the cells may be eluted into RT-PCR mix containing primers for both heavy and light chain genes for multiplex amplification of both genes in a single reaction. Alternatively, the cells may be eluted into RT-PCR mix without primers, the mix may then be split into two equal volume aliquots and the respective heavy and light chain primers may be added to the two aliquots for single-plex amplification. Both methods have been shown to work to amplify the heavy and light chains from a single cell. The exposing the protein produced by the cell to the capture substrate may include flowing a removable capture substrate into the chamber. The method may further include washing the cell prior to flowing a removable capture substrate into the chamber. The protein produced by the cell may be an antigen and the biomolecule may be an antibody. The antibody may be a monoclonal antibody. The biomolecule may be a fluorescently labeled antibody. The fluorescently labeled antibody may be a monoclonal antibody. The determining binding interactions may be a measure of antigen-antibody binding kinetics. The measure of antigen-antibody binding kinetics may be any one or both of: a $K_{on}$ rate; and a $K_{off}$ rate. The APC may be from one of the following: a human, a rabbit, a rat, a mouse, a sheep, an ape, a monkey, a goat; a dog, a cat, a camel, or a pig. The removable capture substrate may be a carboxylic acid (COOH) functionalized bead. The removable capture substrate may be capable of binding the protein produced by the cell and the nucleic acids encoding the protein produced by the cell. The method may further include washing the cell prior to exposing the protein produced by the cell to a capture substrate. The APC may be selected from one of the following: a primary B cell and a memory B cell.

In a further embodiment, there is provided a cell assay method, the method including: distributing an antibody producing cell (APC) to a chamber, wherein the APC is in a first fluid; replacing the first fluid with a second fluid while maintaining the APC in the chamber; placing the antibodies produced by the APC in fluid communication with an antigen; and determining the antigen-antibody binding kinetics of the antibodies produced by the APC with the antigen.

In a further embodiment, there is provided a method of assaying for a binding interaction between a protein produced by a cell and a biomolecule, the method including: (a) retaining the cell within a chamber having an aperture; (b) exposing the protein produced by the cell to a capture substrate, wherein the capture substrate is in fluid communication with the protein produced by the cell and wherein the capture substrate is operable to bind the protein produced by the cell; (c) flowing a fluid volume comprising the biomolecule through the chamber via said aperture, wherein the fluid volume is in fluid communication with the capture substrate; and (d) determining a binding interaction between the protein produced by the cell and the biomolecule.

The measure of antigen-antibody binding kinetics may be the $K_{on}$ rate. The measure of antigen-antibody binding kinetics may be the $K_{off}$ rate. The measure of antigen-antibody binding kinetics may be the both the $K_{on}$ rate and the $K_{off}$ rate. The binding of the antibodies may be further tested by viral inactivation. The binding of the antibodies may be further tested by bacterial inactivation. The binding of the antibodies may be further tested by cell inactivation. The determining of antigen-antibody binding kinetics may be by one or more of the following techniques: surface plasmon resonance (SPR) spectroscopy, fluorescence anisotropy, interferometry, or fluorescence resonance energy transfer (FRET). The determining of antigen-antibody binding kinetics may be by a nanocalorimeter or a nanowire nanosensor. The method may further include adding the cell to a reverse transcription polymerase chain reaction (RT-PCR) reaction to amplify the heavy and light chain genes. The placing the antibodies produced by the APC in fluid communication with an antigen may include flowing a removable capture substrate into the chamber. The method may further include washing the cell prior to flowing a removable capture substrate into the chamber. The APC may be from one of the following: a human, a rabbit, a rat, a mouse, a sheep, an ape, a monkey, a goat; a dog, a cat, a camel, or a pig. The removable capture substrate may be a carboxylic acid (COOH) functionalized bead. The removable capture substrate may be capable of binding the protein produced by the cell and the nucleic acids encoding the protein produced by the cell. The method may further include washing the cell prior to exposing the protein produced by the cell to a capture substrate. The APC may be selected from one of the following: a primary B cell and a memory B cell. The method may further include adding a removable capture substrate to the chamber to capture the antibodies produced by the APC prior to placing the antibodies produced by the APC in fluid communication with an antigen. The placing of the antibodies produced by the APC in fluid communication with an antigen may include flowing a fluorescently labeled antigen through the chamber. The method may further include collecting the mRNA from the cell for a reverse transcription polymerase chain reaction (RT-PCR) reaction to amplify the heavy and light chain genes. The determining the antigen-antibody binding kinetics may include fluorescence imaging of antigen-antibody binding.

In a further embodiment, there is provided a microfluidic device for assaying for a binding interaction between a protein produced by a cell and a biomolecule, the device comprising: a chamber, having: (i) at least one inlet; (ii) at least one outlet; and (iii) a reversible trap having spaced apart structural members extending across the chamber to separate the at least one inlet and at least one outlet wherein the spaced apart structural members are operable to allow fluid flow through the chamber from the inlet to the outlet while providing size selection for a particle within the fluid flow.

In a further embodiment, there is provided a microfluidic device for assaying for a binding interaction between a protein produced by a cell and a biomolecule, the device comprising: a chamber, having: (i) at least one inlet; (ii) at least one outlet; and (iii) a reversible trap, wherein the reversible trap is a narrowing of the chamber from to allow fluid flow through the chamber from the inlet to the outlet while providing size selection for a particle within the fluid flow.

In a further embodiment, there is provided a microfluidic device for assaying a binding interaction between a protein produced by a cell and a biomolecule, the device including: a chamber having an aperture and a channel for receiving a flowed fluid volume through the chamber via said aperture, the channel providing size selection for a particle within said fluid volume.

In a further embodiment, there is provided a microfluidic device for assaying a binding interaction between a protein produced by a cell and a biomolecule, the device including: a chamber having an aperture; a reversible trap having spaced apart structural members extending across the chamber, the structural members being operable to allow a fluid volume to flow through the chamber while providing size selection for a particle within said fluid volume.

The distance between the spaced apart structural members may be less than or equal to about 4.6 microns. The distance between the spaced apart structural members may be less than or equal to about 4.5 microns. The distance between the spaced apart structural members may be less than or equal to about 4.4 microns. The distance between the spaced apart structural members may be less than or equal to about 4.3 microns. The distance between the spaced apart structural members may be less than or equal to about 4.2 microns. The distance between the spaced apart structural members may be less than or equal to about 4.1 microns. The distance between the spaced apart structural members may be less than or equal to about 4.0 microns. The distance between the spaced apart structural members may be less than or equal to about 3.9 microns. The distance between the spaced apart structural members may be less than or equal to about 3.8 microns. The distance between the spaced apart structural members may be less than or equal to about 3.7 microns. The distance between the spaced apart structural members may be less than or equal to about 3.6 microns. The distance between the spaced apart structural members may be less than or equal to about 3.5 microns. The distance between the spaced apart structural members may be less than or equal to about 3.4 microns. The distance between the spaced apart structural members may be less than or equal to about 3.3 microns. The distance between the spaced apart structural members may be less than or equal to about 3.2 microns. The distance between the spaced apart structural members may be less than or equal to about 3.1 microns. The distance between the spaced apart structural members may be less than or equal to about 3.0 microns. The distance between the spaced apart structural members may be less than or equal to about 2.9 microns. The distance between the spaced apart structural members may be less than or equal to about 2.8 microns. The distance between the spaced apart structural members may be less than or equal to about 2.7 microns. The distance between the spaced apart structural members may be less than or equal to about 2.6 microns. The distance between the spaced apart structural members may be less than or equal to about 2.5 microns. The distance between the spaced apart structural members may be less than or equal to about 2.4 microns. The distance between the spaced apart structural members may be less than or equal to about 2.3 microns. The distance between the spaced apart structural members may be less than or equal to about 2.2 microns. The distance between the spaced apart structural members may be less than or equal to about 2.1 microns. The distance between the spaced apart structural members may be less than or equal to about 2.0 microns. The distance between the spaced apart structural members may be less than or equal to about 1.9 microns. The distance between the spaced apart structural members may be less than or equal to about 1.8 microns. The distance between the spaced apart structural members may be less than or equal to about 1.7 microns. The distance between the spaced apart structural members may be less than or equal to about 1.6 microns. The distance between the spaced apart structural members may be less than or equal to about 1.5 microns. The distance between the spaced apart structural members may be less than or equal to about 1.4 microns. The distance between the spaced apart structural members may be less than or equal to about 1.3 microns. The distance between the spaced apart structural members may be less than or equal to about 1.2 microns. The distance between the spaced apart structural members may be less than or equal to about 1.1 microns. The distance between the spaced apart structural members may be less than or equal to about 1.0 microns. The distance between the spaced apart structural members may be less than or equal to about 0.9 microns. The distance between the spaced apart structural members may be less than or equal to about 0.8 microns. The distance between the spaced apart structural members may be less than or equal to about 0.7 microns. The distance between the spaced apart structural members may be less than or equal to about 0.6 microns. The distance between the spaced apart structural members may be less than or equal to about 0.5 microns. The spaced apart structural members may be posts. The spaced apart structural members may be between 5 to 30 microns in width. The spaced apart structural members may be between 10 to 20 microns in width. The spaced apart structural members may be between 5 to 30 microns in width. The spaced apart structural members may be between 5 to 20 microns in width. The spaced apart structural members may be between 5 to 10 microns in width.

The narrowing of the chamber may be from greater than about 10 microns to less than about 5.0 microns. The narrowing of the chamber may be from greater than about 10 microns to less than about 4.9 microns. The narrowing of the chamber may be from greater than about 10 microns to less than about 4.8 microns. The narrowing of the chamber may be from greater than about 10 microns to less than about 4.7 microns. The narrowing of the chamber may be from greater than about 10 microns to less than about 4.6 microns. The narrowing of the chamber may be from greater than about 10 microns to less than about 4.5 microns. The narrowing of the chamber may be from greater than about 10 microns to less than about 4.4 microns. The narrowing of the chamber may be from greater than about 10 microns to less than about 4.3 microns. The narrowing of the chamber may be from greater than about 10 microns to less than about 4.2 microns. The narrowing of the chamber may be from greater than about 10 microns to less than about 4.1 microns. The narrowing of the chamber may be from greater than about 10 microns to less than about 4.0 microns.

It will be appreciated by a person of skill in the art that the distance between the spaced apart structural members and the narrowing of the chamber to produce the reversible trap, will depend on the size of the cells being assayed and the size of the removable capture substrate, and the flow velocity through the chamber, whereby the cell and the removable capture substrate are retained in the chamber at a first flow velocity and whereby the removable capture substrate is retained in the chamber and the cell is able to deform and fit through the reversible trap at a second flow velocity. Alternatively, there may be different sized removable capture substrates and some may be permitted to pass through the reversible trap, while other may be retained. Furthermore, there may be further flow velocities possible with a given device, whereby the reversible trap may deform to allow the removable capture substrates to pass through the chamber. Alternatively, the chamber may be pierced to remove the removable substrate and/or cells. The narrowing of the chamber may correspond to the channel size selection.

The particle may be selected from one or more of the cell, the biomolecule, the protein, the protein bound to a removeable capture substrate, and the removeable capture substrate. The size selection of the reversible trap may prevent the cell and the removeable capture substrate from passing through the reversible trap, and may allow the biomolecule and the protein to pass through the reversible trap at a first flow velocity, and the size selection of the reversible trap may prevent the removeable capture substrate from passing through the reversible trap, while allowing the cell, the biomolecule and the protein to pass through the reversible trap at a second flow velocity. The outlet may be a sieve valve and the flow velocity through the chamber when the valve is in an open position may be sufficient to allow the cell to deform and pass through the reversible trap. The device may be operable to provide two or more flow velocities through the chamber. The device may be operable to provide two flow velocities through the chamber. The device may be operable to provide three flow velocities through the chamber. The device may be operable to provide four flow velocities through the chamber. The microfluidic device may be operable to allow for removal of the removeable capture substrate. The microfluidic device may be operable to allow for removal of the cell.

The cells get trapped in the chambers when the sieve valves are closed. However, as with the posts, the cells deform when the sieve valve is opened and there is increased flow through the chambers. Both implementations of the reversible trap have worked, but the bead post design is slightly more robust at retaining the beads. The cells being used in the present experiments are about 10 microns in diameter, the beads are 5 microns in diameter, and the space between the posts is less than 3 microns.

A chamber may be in fluid communication with a first auxiliary chamber, wherein there is may be a valve between the chamber and the first auxiliary chamber. The first auxiliary chamber may be in fluid communication with a second auxiliary chamber, wherein there is a valve between the first and second auxiliary chambers, wherein the valve has an open position to allow fluid flow from the first auxiliary chamber to the second auxiliary chamber and a closed position to prevent fluid flow from the first auxiliary chamber to the second auxiliary chamber. The first auxiliary chamber may be in fluid communication with a second auxiliary chamber and the second auxiliary chamber is in fluid communication with a third auxiliary chamber, wherein there is a valve between the first and second auxiliary chambers, wherein the valve has an open position to allow fluid flow from the first auxiliary chamber to the second auxiliary chamber and a closed position to prevent fluid flow from the first auxiliary chamber to the second auxiliary chamber, wherein there is a valve between the second and third auxiliary chambers, wherein the valve has an open position to allow fluid flow from the second auxiliary chamber to the third auxiliary chamber and a closed position to prevent fluid flow from the second auxiliary chamber to the third auxiliary chamber. The volumes of the first second and third auxiliary chambers relative to the chamber may be such that fluid may be flowed into these chambers such that subsequent RT and PCR or other reactions may be carried out without exchanging the fluid (for example, where a first outlet is in a closed position).

The volume of the auxiliary chambers may be expandable. The volume of the chamber may be between 0.1 nL to 100.0 nL. The unexpanded volume of the expandable the chamber may be between 0.1 nL to 100.0 nL. The volume of the chamber may be 0.6 nL. The unexpanded chamber may be 0.6 nL. The effective volume of a given chamber may be increased by expanding the initial chamber or by opening a valve to provide fluid flow into one or more auxiliary chambers. The ratio between the second auxiliary chamber and the first auxiliary chamber may be 5:1. The ratio between the second auxiliary chamber and the first auxiliary chamber may be at least 5:1. The ratio between the expanded chamber and the unexpanded chamber may be 5:1 or the ratio between the expanded first auxiliary chamber unexpanded first auxiliary chamber may be 5:1. The ratio between the expanded chamber and the unexpanded chamber may be at least 5:1 or the ratio between the expanded first auxiliary chamber unexpanded first auxiliary chamber may be at least 5:1. The ratio between the second auxiliary chamber and the first auxiliary chamber, or between the expanded chamber and the unexpanded chamber, or between the expanded first auxiliary chamber unexpanded first auxiliary chamber may vary depending on the reaction mixtures chosen, the concentrations of the components of the mixture and the concentration of the material being assayed. Alternatively, the chamber may be between 0.05 nL and 100.0 nL. Alternatively, the chamber may be between 0.05 nL and 90.0 nL. Alternatively, the chamber may be between 0.1 nL and 95.0 nL. Alternatively, the chamber may be between 0.1 nL and 90.0 nL. Alternatively, the chamber may be between 0.1 nL and 85.0 nL. Alternatively, the chamber may be between 0.1 nL and 80.0 nL. Alternatively, the chamber may be between 0.1 nL and 75.0 nL. Alternatively, the chamber may be between 0.1 nL and 70.0 nL. Alternatively, the chamber may be between 0.1 nL and 65.0 nL. Alternatively, the chamber may be between 0.1 nL and 60.0 nL. Alternatively, the chamber may be between 0.1 nL and 55.0 nL. Alternatively, the chamber may be between 0.1 nL and 50.0 nL. Alternatively, the chamber may be between 0.1 nL and 45.0 nL. Alternatively, the chamber may be between 0.1 nL and 40.0 nL. Alternatively, the chamber may be between 0.1 nL and 35.0 nL. Alternatively, the chamber may be between 0.1 nL and 30.0 nL. Alternatively, the chamber may be between 0.1 nL and 25.0 nL. Alternatively, the chamber may be between 0.1 nL and 20.0 nL. Alternatively, the chamber may be between 0.1 nL and 15.0 nL. Alternatively, the chamber may be between 0.1 nL and 10.0 nL. Alternatively, the chamber may be between 0.1 nL and 9.0 nL. Alternatively, the chamber may be between 0.1 nL and 8.0 nL. Alternatively, the chamber may be between 0.1 nL and 7.0 nL. Alternatively, the chamber may be between 0.1 nL and 6.0 nL. Alternatively, the chamber may be between 0.1 nL and 5.0 nL. Alternatively, the chamber may be between 0.1 nL and 4.0 nL. Alternatively, the chamber may be between 0.1 nL and 3.0 nL. Alternatively, the chamber may be between 0.1 nL and 2.0 nL. Alternatively, the chamber may be between 0.1 nL and 1.0 nL.

In a further embodiment, there is provided a method of assaying for a protein of interest produced by a cell, the method comprising: incubating the cell with a removable capture substrate in a buffer, wherein the removable capture substrate is capable of binding the protein of interest and nucleic acids encoding the protein of interest; and screening the bound removable capture substrate to determine whether the cell produces the protein of interest.

In a further embodiment, there is provided a method of assaying for a protein of interest produced by a cell, the method comprising: incubating the cell with a removable capture substrate in a buffer, wherein the removable capture substrate is capable of binding the protein of interest; and screening the bound removable capture substrate to determine whether the cell produces the protein of interest.

In a further embodiment, there is provided a method of identifying a monoclonal antibody of interest, the method comprising: incubating an APC with a removable capture substrate in a suitable buffer, wherein the removable capture substrate is capable of binding the monoclonal antibody produced by the APC and nucleic acids encoding the variable regions of the monoclonal antibody; and screening the bound removable capture substrate to determine whether the APC produces the monoclonal antibody of interest.

In a further embodiment, there is provided a cell assay method, the method comprising: distributing an APC to a chamber, wherein there is on average one APC in the chamber, wherein the APC is incubated with a removable capture substrate in a first solution, and wherein the removable capture substrate is capable of binding an antibody of interest produced by the APC and nucleic acids encoding the variable regions of the antibody of interest; replacing the first solution with a second solution while maintaining the APC in the chamber; placing the antibody of interest produced by the APC in fluid communication with an antigen; and screening the bound removable capture substrate to determine whether the APC produces the antibody of interest.

In a further embodiment, there is provided a method of assaying for a chemical interaction between a protein produced by a cell and a biomolecule, the method comprising: distributing the cell to a chamber, wherein the cell is in a first solution; replacing the first solution with a second solution while maintaining the cell in the chamber; placing the protein in fluid communication with the biomolecule; and testing the chemical interaction of the protein produced by the cell with the biomolecule.

In a further embodiment, there is provided a method of identifying a monoclonal antibody of interest, the method comprising: incubating an antibody producing cell (APC) with a removable capture substrate in a suitable buffer, wherein the removable capture substrate is capable of binding the monoclonal antibody produced by the APC and nucleic acids encoding the variable regions of the monoclonal antibody; and screening the bound removable capture substrate to determine whether the APC produces the monoclonal antibody of interest.

In a further embodiment, there is provided a cell assay method, the method comprising: distributing an antibody producing cell (APC) to a chamber, wherein there is on average one APC in the chamber, wherein the APC is incubated with a removable capture substrate in a first solution, and wherein the removable capture substrate is capable of binding an antibody of interest produced by the APC and nucleic acids encoding the variable regions of the antibody of interest; replacing the first solution with a second solution while maintaining the APC in the chamber; placing the antibody of interest produced by the APC in fluid communication with an antigen; and screening the bound removable capture substrate to determine whether the APC produces the antibody of interest.

In a further embodiment, there is provided a method of assaying for a protein of interest produced by a cell. The method involves incubating the cell with a removable capture substrate in a suitable buffer, wherein the removable capture substrate is capable of binding the protein of interest; and screening the bound removable capture substrate to determine whether the cell produces the protein of interest.

The method may involve determining the binding affinity of the protein of interest. The method may involve determining a dissociation rate; and association rate and dissociation rate.

The method may involve lysing the cell prior to incubation with the removable capture substrate, wherein the protein of interest is not secreted by the cell.

In a further embodiment, there is provided a device for selecting a cell that produces a protein having a binding affinity for a biomolecule. The device may include a microfluidic device as described herein operably configured to hold an aliquot, wherein the aliquot on average contains one cell, and wherein the protein produced by the cell is in fluid communication with the biomolecule; and a detector for detecting the binding affinity of the protein produced by the cell.

The device may include a detector that is a fluorescence imager for detecting the binding affinity. The device may include a detector that is a surface plasmon resonance (SPR) spectroscopy apparatus, or a fluorescence anisotropy apparatus, or an interferometry apparatus, or a FRET apparatus. Further, the device may include a detector that is a nanocalorimeter or a nanowire nanosensor.

In a further embodiment, there is provided a kit for identifying a cell that produces antibodies having a binding affinity for an antigen. The kit includes a microfluidic device as contemplated herein; and a removable capture substrate. The kit may include the removable capture substrate being capable of binding proteins, or nucleic acids, or proteins and nucleic acids. The kit may include the removable capture substrate being a microsphere. Further, the kit may include the microsphere being a polystyrene bead or a silica bead. Further, the kit may include the microsphere being a carboxylic acid (COOH) functionalized bead.

The kit may include an antigen label. The kit may include an antigen label that is a fluorescent label. Further, the kit may include instructions for the use of the device contemplated herein to identify a cell that produces proteins having a desired binding affinity. Further, the kit may include instructions for immunizing an animal and collecting APCs. Further, the kit may include an antigen.

BRIEF DESCRIPTION OF THE DRAWINGS

FIG. 1A is an illustration of a microfluidic device containing control channels for individually selecting six reagent inlets and actuating sieve valves on the reagent outlet channel. FIG. 1B shows a microscopic image of the device with food coloring to visualize distinct reagent inlets (as shown) and control channels (as shown) (5× magnification); Top inset depicts a close-up of beads trapped using sieve valves (20× magnification; Bottom inset depicts fluorescence image of beads during binding kinetic measurements (100× magnification). FIG. 1C shows a schematic of a bead assay for direct measurement of association and dissociation kinetics of immobilized mAbs and fluorescently-labeled antigen. FIG. 1D shows a variation of a bead assay for indirect measurement of dissociation kinetics of immobilized mAbs and unlabeled antigen molecules.

FIG. 2A: Hydraulic pressure is applied to valves (fully-closing) and sieve valves (partially-closing) formed by the intersection of actuation control channels with rounded- or square-profile flow channels, respectively. FIGS. 2B-2H: An expanded view of an embodiment of a microfluidic device for the detection of antibody secreted from single cells. FIG. 2B: (1) chip is flushed with 1×PBS; FIG. 2C: (2) antibody-secreting cells and antibody-capture beads are loaded into chambers; FIG. 2D: (3) cells are incubated for one hour to allow for antibody secretion; FIG. 2E: (4) mix valve is opened to allow for secreted antibody to bind to beads; FIG. 2F: (5) beads and cells are captured against sieve valve and unbound antibody is washed out; FIG. 2G: (6) chambers flushed with fluorescently-labeled antigen; image and measure antibody-antigen association kinetics; and FIG. 2H: (7) flushed out unbound antigen with 1×PBS; image and measure antibody-antigen dissociation kinetics.

FIG. 3B: HyHEL-5 mAb and HEL-Dylight488 conjugate, FIG. 3C: LGB-1 mAb and enhanced green fluorescent protein (EGFP) are demonstrated. FIG. 3D: Indirect measurement of dissociation kinetics of D1.3 mAb and HEL using HEL-Dylight488 conjugate is demonstrated.

FIG. 4A: Plots measured association and dissociation kinetics of 3 distinct mAbs (HyHEL-5, D1.3, and LGB-1 mAb) interacting with 2 different antigens (HEL-Dylight633 conjugate and EGFP) is demonstrated. FIG. 4B: A micrograph showing false-coloured, overlay of images taken with distinct fluorescence filter cubes to identify anti-lysozyme mAbs and anti-EGFP mAbs is demonstrated.

FIG. 5A: Measured association kinetics of D1.3 mAb-Dylight488 conjugate on rabbit anti-mouse pAb coated beads is demonstrated. Inset demonstrates a schematic of bead assay for measuring binding kinetics of fluorescently-labeled mouse mAb and rabbit anti-mouse pAb coated beads. FIG. 5B: Association kinetics of HEL-Dylight488 conjugate on beads with varying amounts of immobilized D1.3 mAb is demonstrated. FIG. 5C: Equilibrium bead fluorescence varies linearly with the amount of immobilized D1.3 mAb. Inset shows a close-up of the graph to highlight detection limit of 1% bead coverage. FIG. 5D: Direct measurement of equilibrium dissociation constants by measuring equilibrium bead fluorescence using immobilized D1.3 mAb and varying concentrations of HEL-Dylight488.

FIG. 6A: Microscope image of D1.3 hybridoma cell loaded into a microfluidic device adjacent to rabbit anti-mouse pAb coated beads trapped using a sieve valve is shown. FIG. 6B: "Single-cycle" binding kinetics from a single bead containing D1.3 mAbs secreted from a single cell and subject to increasing concentrations of HEL-Dylight488 conjugate is demonstrated.

FIG. 7A: Photobleaching rates of fluorescent dye molecules under 100 W Hg lamp illumination using 100× oil-immersion objective (NA 1.30) are plotted. FIG. 7B: Effect of fluorescent exposure times on measured association kinetics of D1.3 mAb and HEL-Dylight488 are plotted.

FIGS. 12A-12C show representative microscopic images of primary ASCs in a microfluidic chamber in fluid communication with antibody capture beads and oligo(dT) beads.

FIG. 13A: The left image represents cells that secreted any antibody; FIG. 13B: the right image represents only those cells that secreted HEL-specific antibodies.

FIG. 15A: Brightfield image of dual-function beads trapped using microfluidic sieve valve. FIG. 15B: Fluorescence image of synthetic single-stranded DNA molecules captured on dual-function beads. Synthetic DNA molecules are labeled with Cy5 fluorophore for visualization and also contain a poly(A) tail that binds to the oligo(dT) on the bead surface. FIG. 15C: Fluorescence image of mouse D1.3 monoclonal antibody (mAb) captured on dual-function beads. D1.3 mAbs are labeled with Dylight488 fluorophore for visualization and bind to the Rabbit anti-Mouse pAb on the bead surface.

FIG. 16A: a microscopic image and FIG. 16B: antibody-antigen binding kinetics as determined from a microfluidic device for dual purpose beads.

FIG. 17A: $K_d$, FIG. 17B: $K_{on}$, and FIG. 17C: $K_{off}$ rates determined from specific eluted chambers according to Example 9 herein.

FIG. 18A: depicts data for R00C04; FIG. 18B: depicts data for R04C06.

FIG. 20A: brightfield image at 20× magnification; FIG. 20B: brightfield image at 40× magnification.

FIG. 21A: (1) Flush chip with 1×PBS; FIG. 21B: (2) Load antibody-secreting cells into chambers; FIG. 21C: (3) Load antibody-capture beads into inlet channel; FIG. 21D: (4) Load antibody-capture beads into chamber against bead filter; FIG. 21E: (5) Incubate cells for 1 hour to allow antibody secretion and capture on beads; FIG. 21F: (6) Wash out unbound antibody; FIG. 21G: (7) Load fluorescently-labeled antigen into inlet channel; FIG. 21H: (8) Flush chambers with fluorescently-labeled antigen; image and measure antibody-antigen association kinetics; FIG. 21I: (9) Flush our unbound antigen with 1×PBS; image and measure antibody-antigen dissociation kinetics; and FIG. 21J: (10) Open sieve valve and flush cell out of the chamber to the elution port for recovery from device.

DETAILED DESCRIPTION

Figure 1A:
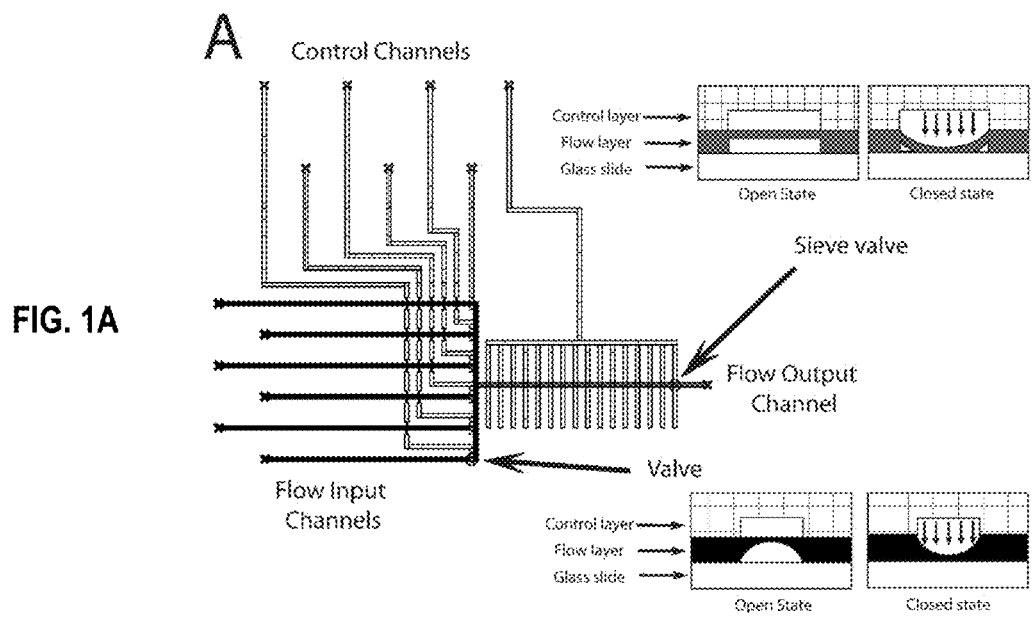
FIGS. 1A-1D show a microfluidic device and schematics for bead-based measurements of antibody-antigen binding kinetics.
Figure 1B:
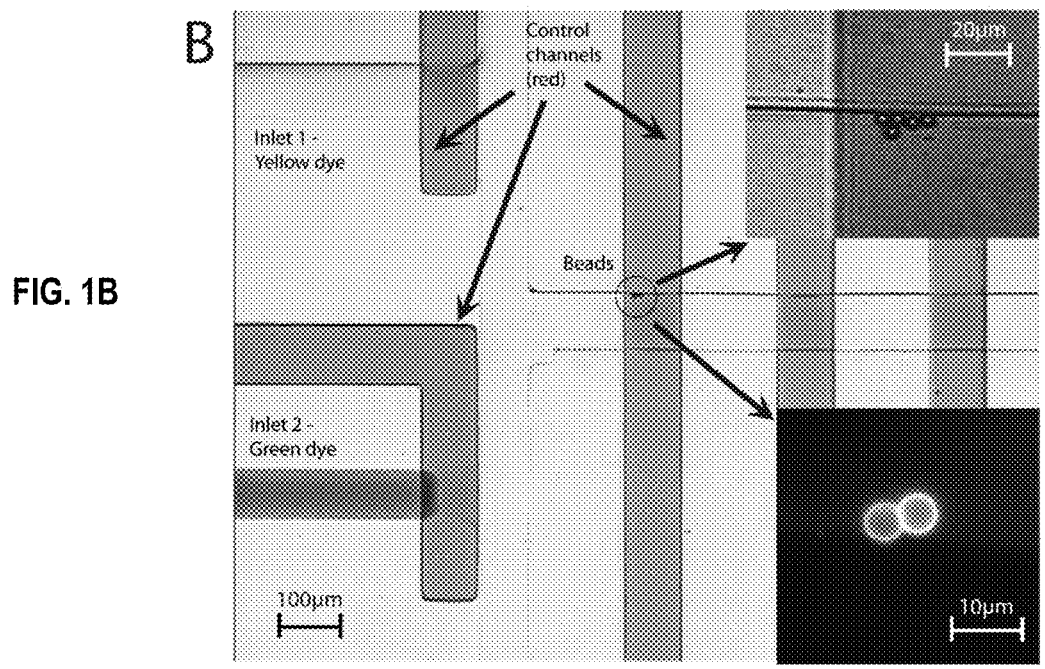

A binding interaction, as referred to herein, includes a molecular interaction. A molecular interaction is commonly understood as referring to a situation when two or more molecules are attracted to one another by a force, where the force could be for example, electrostatic, dipole-dipole, hydrogen bonding, covalent, or hydrophobic in nature. A binding affinity is commonly understood as referring to an average strength of a molecular interaction. Similarly, "avidity" is used to describe the combined strength of multiple interactions. When used in the present application, "affinity" is meant to encompass one or more interactions, including avidity. The methods described herein may involve determining the binding affinity of the protein of interest. The methods described herein may also involve determining a dissociation rate; and association rate and dissociation rate. Alternatively, the methods described herein may include determining binding kinetics.

The method may involve testing the antigen binding affinity by fluorescence imaging. The method may involve testing the antigen binding affinity using any of the following techniques plasmon resonance (SPR) spectroscopy, fluorescence anisotropy, or interferometry. These techniques are understood to measure antibody-antigen binding kinetics, including, but not limited to surface plasmon resonance (SPR) spectroscopy, fluorescence anisotropy, interferometry, or fluorescence resonance energy transfer (FRET). See, for e.g., Bornhop et al. (2007), *Science* 317: 1732-1736; Homola et al. (1999) *Sensors and Actuators B: Chemical* 54: 3-15; and Xavier, K. A. and Willson, R. C. (1998), *Biophys. J.* 74: 2036-2045. Further, the method may involve testing the antigen binding affinity by a nanocalorimeter or a nanowire nanosensor. See, for e.g., Wang et al. (2005), *Proc. Natl. Acad. Sci. USA* 102: 3208-3212 and Lee et al. (2009) *Proc. Natl. Acad. Sci. USA* 106: 15225-15230. Another method that could be employed would be to use a technique such as dark-field microscopy and use antigens or antibodies labeled with gold nanoparticles. This could be used to detect single molecules and generate on/off rates by counting the molecules. See, for e.g., Ueno et al. (2010) *Biophysical J.* 98: 2014-2023; Raschke et al. (2003) *Nano Letters* 3: 935-938; and Sonnischen et al. (2000) *App. Phys. Letters* 77: 2949-2951. Further methods for labeling and detecting binding events and/or binding kinetics would be known to a person of skill in the art. For example, binding assays may include determining the number of binding events.

A protein, as referred to herein, refers to organic compounds made of amino acids, including both standard and non-standard amino acids. Standard amino acids include the following: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine. An example of a protein is an antibody.

A biomolecule, as referred to herein, may include, but is not limited to, an antibody, or an antibody fragment, or a whole cell, or a cell fragment, or a bacterium, or a virus, or a viral fragment, a nucleic acid or a protein.

A "chamber", as used herein, refers to an enclosed space within a microfluidic device in which a cells may be retained. Each chamber may have at least one inlet for permitting fluid, including fluid containing a cell, to enter the chamber, and at least one outlet to permit fluid and/or the cell to exit the chamber (depending on the design of the chamber and/or the flow through the chamber). Persons skilled in the art will understand that an inlet or an outlet can vary considerably in terms of structure and dimension, and may be characterized in a most general sense as an aperture that can be reversibly switched between an open position, to permit fluid to flow into or out of the chamber, and a closed position to seal the chamber and thereby isolate and retain its contents. Alternatively, the aperture may also be intermediate between the open and closed positions to allow some fluid flow or may be a sieve valve that allows for fluid flow out of the cell, but not other particles (for example, the cell, the beads etc.). A chamber, as referred to herein, refers to a portion of a microfluidic device which is designed to hold, for example, a cell. As used herein, the chamber is of an exceptionally small and discrete sizing. Typical volumes are in the range of ~100 µl to ~100 nl. For example, a chamber can be designed with a volume of approximately 500 pL (less than 1 nL), with dimensions of approximately 100 microns (width), 500 microns (length), and 10 microns (height).

The direction of fluid flow through the chamber dictates an "upstream" and a "downstream" orientation of the chamber. Accordingly, an inlet will be located at an upstream position of the chamber, and an outlet will be generally located at a downstream position of the chamber. A person skilled in the art will understand, however, that a single aperture could function as both an inlet and an outlet.

An "inlet" or an "outlet", as used herein, may include any aperture whereby fluid flow is restricted through the inlet or outlet. There may be a valve to control flow, or flow may be controlled by separating the channels with a layer which prevents flow (for example, oil). Alternatively, an aperture may serve as both an inlet and outlet. Furthermore, an aperture (i.e. inlet or outlet) as used herein is meant to exclude the surface opening of a microwell.

A "microfluidic device", as used herein, refers to any device that allows for the precise control and manipulation of fluids in a geometrically constrained structure. For example, where at least one dimension of the structure (width, length, height) is less than 1 mm.

A solution, as referred to herein, may include, but is not limited to, a solution that can maintain the viability of a cell. Further, the solution may include a suitable buffer that can both retain the viability of a cell such that binding interactions can be obtained or allow for an effective lysis of the cell to obtain nucleic acids from the cell and/or antibodies or other proteins depending on the application. Alternatively, the solution may be suitable for performing an assay.

A capture substrate, as referred to herein, is meant to encompass a wide range of substrates capable of capturing a protein or biomolecule of interest. These substrates may be modified to alter their surface (internal and external) properties depending on the desired use. For example, a substrate may be bound to antibodies or antigens to capture an antibody of interest. A capture substrate may be, for example, a microsphere or a nanosphere or other microparticles including, but not limited to a polystyrene bead or a silica bead (for example, antibody capture beads and oligo (dT) mRNA capture beads). In an alternate arrangement, instead of modifying the beads with oligo(dT), specific primers could be utilized instead.

Optionally, the microsphere may be a carboxylic acid (COOH) functionalized bead. Beads which make use of alternate chemical interactions can fall within this definition. See: for e.g., G. T. Hermanson (2008), *Bioconjugate Techniques*, 2nd Edition, Published by Academic Press, Inc. For example, an alternate scheme for preparing these beads would be to use streptavidin coated beads and to mix these beads with biotinylized rabbit anti-mouse pAbs and biotinylated oligo(dT). A capture substrate can also be an anti-Ig bead which binds an antibody to the capture substrate. A capture substrate can be modified such that it binds multiple biomolecules of interest, for example both mRNA and protein. Alternately, each capture substrate could be limited to a particular biomolecule, for example, one capture substrate being limited to binding mRNA and a second capture substrate being limited to binding a protein. Capture substrates are commercially available or may be made de novo and/or modified as needed for the particular application. Capture substrates may be removable, as in the case of beads. However, capture substrates may also be fixed (and thus, non-removable).

Nucleic acids, as referred to herein, include macromolecules composed of chains of monomeric nucleotides. Common examples of nucleic acids include deoxyribonucleic acid (DNA) and ribonucleic acid (RNA).

In a further embodiment, a cell assay method is provided. The method involves distributing an antibody producing cell (APC) to a chamber, wherein the APC is in a first solution, and wherein there is on average one APC in the chamber; replacing the first solution with a second solution while maintaining the APC in the chamber; placing the antibodies produced by the APC in fluid communication with an antigen; and testing the binding of the antibodies produced by the APC with the antigen. Optionally, the method may involve adding anti-Ig beads to the chamber to capture the antibodies produced by the APC. Optionally, the method may involve lysing the APC to capture antibodies produced by the APC wherein the antibodies are not secreted by the APC.

A cell as referred to herein includes an antibody producing cell (also referred to herein as an "APC"). An APC refers to a cell that can produce an antibody. An antibody producing cell is not limited to cells that secrete antibodies, which are also referred to herein as antibody secreting cells (also referred to herein as an "ASC"). For example, it will be understood from the relevant art that memory B cells, without stimulation, do not normally secrete antibodies. See, for e.g., Abbas et al. (1997), *Cellular and Molecular Immunology*, $3^{rd}$ Ed., pp. 22-23). Examples of antibody producing cells (APCs) include B cells, memory B cells, primary B cells (which are also known in the art as naïve B cells), and B cell hybridomas. A primary B cell can be harvested from the spleen, blood, or bone marrow of an animal, for example from a mouse, by FACS sorting for a cell surface marker, for example, the CD138+ marker (See: for e.g., Smith et al. (1996) *Eur. J. Immunol.* 26: 444-448).

Antibodies are defense proteins produced by the vertebrate adaptive immune system for the purposes of binding and targeting for clearance a diverse range of bacteria, viruses, and other foreign molecules (antigens). As a result of their ability to bind target antigens selectively and with high affinity, antibodies are invaluable tools for protein purification, cell sorting, and diagnostics. Antibodies are produced by B cells and are secreted by activated B cells. (See generally, for e.g., Abbas et al. (1997), *Cellular and Molecular Immunology*, $3^{rd}$ Ed., Chapter 3, pp. 37-65). Antibodies are also referred to herein as immunoglobulin (also referred to herein as Ig). An antibody, as referred to herein, can include, but is not limited to polyclonal antibodies and monoclonal antibodies. Unlike polyclonal antibodies, monoclonal antibodies are monospecific antibodies that are the same because they are made by one type of immune cell that are all clones of a unique parent cell. A single APC or ASC can serve as the source of a monoclonal antibody. Antibodies are not limited to a specific isotype and can include, but are not limited to the following isotypes: IgM, IgG, IgD, IgE, and IgA. Typically, it is understood that antibodies are comprised of light and heavy chains that have variable and constant regions therein (see generally, for e.g., Abbas et al. (1997), *Cellular and Molecular Immunology*, $3^{rd}$ Ed., Chapter 3, pp. 37-65).

In a further embodiment, a method of identifying a monoclonal antibody of interest is provided. The method involves incubating an APC with a removable capture substrate (RCS) in a suitable buffer, wherein the removable capture substrate is capable of binding the monoclonal antibody produced by the APC and nucleic acids encoding the variable regions of the monoclonal antibody; and screening the bound removable capture substrate to determine whether the APC produces the monoclonal antibody of interest.

In a further embodiment, a cell assay method is provided. The method involves distributing an APC to a chamber, wherein there is on average one APC in the chamber, wherein the APC is incubated with a removable capture substrate in a first solution, and wherein the removable capture substrate is capable of binding an antibody of interest produced by the APC and nucleic acids encoding the variable regions of the antibody of interest; replacing the first solution with a second solution while maintaining the APC in the chamber; placing the antibody of interest produced by the APC in fluid communication with an antigen; and screening the bound removable capture substrate to determine whether the APC produces the antibody of interest.

In a further embodiment an apparatus for selecting a cell that produces a protein having a binding affinity for a biomolecule is provided. The apparatus includes a microfluidic device operably configured to hold an aliquot, wherein the aliquot on average contains one cell, and wherein the protein produced by the cell is in fluid communication with the biomolecule; and a detector for detecting the binding affinity of the protein produced by the cell. However, the microfluidic device may also hold more than one cell, particular in an assay where the antigen or biomolecule of interest is a cell, or a cell fragment. Similarly, the antigen may be a virus or a bacterial cell.

In a further embodiment, a kit for identifying a cell that produces antibodies having a binding affinity for an antigen is provided. The kit includes a microfluidic device and a removable capture substrate.

An antigen, as referred to herein, refers to a molecule recognized by the immune system. As such, an antigen can include a molecule that can elicit an immune response in an organism, including in an animal. Examples of antigens include, but are not limited to bacterial antigens and viral antigens.

A method is provided for identifying antibody secreting cells (ASCs) that produce antibodies having a particular binding affinity for an antigen or functional attributes. The method involves distributing an ASC within a discrete aliquot wherein there is on average one ASC in the aliquot, placing the antibodies in fluid communication with the antigen; and testing the antigen binding affinity of the antibodies produced by the ASC. The method is based in part on the discovery that a single ASC, without clonal expansion, is capable of producing enough antibodies to test binding affinity for an antigen or to test other functional attributes. Furthermore, the method is also based, in part, on the discovery that clonal expansion via the production of hybridomas is not required for larger scale production of monoclonal antibodies, whereby the variable regions for the antibodies of interest may be sequenced from an ASC of interest or collected with antibodies.

By way of example, a sensitive, low-cost microfluidic bead-based fluorescence assay is described herein for measuring antibody-antigen binding kinetics within low abundance samples. Direct measurements of antibody-antigen binding kinetics may be made by time-course fluorescence microscopy of antibody-conjugated beads retained in microfluidic chambers and subject to a series of wash cycles with fluorescently-labeled antigen and buffer. A variation of the bead-based assay may include measuring the dissociation kinetics of unlabeled antibody and antigen molecules. As disclosed herein, multiple antibody-antigen interactions were measured spanning nearly four orders of magnitude in equilibrium binding affinity. The rate constants measured by way of the assay disclosed herein were validated with previously published values using SPR spectroscopy.

The methods provided herein are also contemplated for being used to screen mutagenic B cell lines. Further, the methods provided herein are contemplated for being used to screen the selectivity and specificity of antibodies to multiple different antigens.

Antibody Binding Kinetics

The affinity or binding strength of an antibody for its target antigen is an important parameter when selecting an antibody for a given application. Although the affinity of an antibody-antigen interaction is typically quantified by an equilibrium binding constant ($K_d$), which describes the dynamic equilibrium between binding and unbinding events, the kinetic rate constants ($k_{on}$ and $k_{off}$) provide a more complete characterization of an antibody-antigen interaction. Two antibodies with identical $K_d$ values may exhibit dramatically different binding kinetics which, in turn, will determine their respective suitability for a given application. For instance, antibodies with rapid association and dissociation kinetics may be desirable for sensing applications, whereas antibody-antigen interactions with very long half-lives may be critical for histological staining, enzyme-linked immunosorbent assays (ELISA), and Western blotting. Similarly, therapeutic antibodies that bind their target antigens with long half-lives could, in principle, be administered in lower dosages, reducing the cost and side-effects of these therapies. Direct measurement of binding kinetic constants can be a critical factor for selecting antibodies for both clinical and research applications. Examples of kinetic assays include, but are not limited to viral and other pathogenic neutralization, cell signaling and growth inhibition, modulation of enzymatic activity (inhibit or enhance).

Microfluidics

Microfluidics refers to a multidisciplinary field dedicated to the design of systems in which small volumes of fluids will be used for a variety of purposes, including lab-on-a-chip technology. See: for e.g., Squires and Quake (2005), *Reviews of Modern Physics* 77: 977-1026. Microfluidic technologies enable small-scale (picoliter to nanoliter) fluid handling operations for high-throughput biochemical analyses with low reagent costs and rapid analysis times. In particular, microfluidic devices fabricated from a silicone rubber, polydimethylsiloxane (PDMS), can be designed and fabricated in 24-48 hours, enabling rapid prototyping of devices. See: for e.g., McDonald, J. C. et al. (2000), *Electrophoresis* 21: 27-40. Microfluidic devices that integrate valves into pumps, mixers, fluidic multiplexers (MUXes), and other fluid-handling components have been successfully applied for protein crystallization, chemical synthesis, protein and DNA detection and single cell analysis. See, for e.g., Thorsen et al. (2002), *Science* 298: 580-584; Hansen, et al. (2002), *Proc. Natl. Acad. Sci. USA* 99: 16531-16536; Maerkl, S. J. & Quake, S. R. (2007) *Science* 315: 233-237; Hansen et al. (2004), *Proc. Natl. Acad. Sci. USA* 101, 14431-14436; Huang, B. et al. (2007) *Science* 315, 81-84; and Cai et al. (2006) *Nature* 440: 358-362. Microfluidic devices, as described herein, can include chambers of varying sizes. For example, chambers can be designed with a volume of approximately 500 pL (less than 1 nL), with dimensions of approximately 100 microns (width), 500 microns (length), and 10 microns (height).

As disclosed herein, antibody-antigen binding kinetics were measured with approximately $4 \times 10^4$ antibody molecules (~66 zeptomoles) immobilized on a single bead and less than $2 \times 10^6$ antibodies (~3 attomoles) loaded into the microfluidic device. This represents a reduction of greater than four orders of magnitude in both detection limit and sample consumption compared to SPR spectroscopy and a recently reported microfluidic fluorescence assay for measuring protein-protein binding kinetics. See, for e.g., Bates, S. R.; Quake, S. R. (2009), *Appl. Phys. Lett.* 95, 073705. Since each antibody-antigen interaction can be characterized on a single bead, millions of distinct antibody-antigen interactions can be characterized with a single lot of commercially available beads (i.e., 1 mL at $10^7$-$10^8$ beads/mL). By using the bead surface rather than the chip surface as the sensor, a single microfluidic device may be re-used indefinitely and may be imaged using a standard inverted fluorescence microscope. However, a person of skill in the art could also apply the basic methods described herein to a microfluidic system having antigen and/or antibodies bound to the surface of a chip. It is further shown herein that an assay applying a method described herein may be used to perform simultaneous kinetic measurements of multiple antibody-antigen interactions using spatial and optical multiplexing. By comparison, characterization of each antibody-antigen interaction using SPR spectroscopy requires specialized instrumentation and a unique flow cell on comparatively expensive sensor chips. The low detection limit of the microfluidic bead assay coupled with small volume compartmentalization was exploited in order to measure the antigen binding kinetics of antibodies secreted by a single ASC. It is contemplated that the microfluidic bead assay described herein could be used for measuring antibody-antigen binding kinetics from rare blood samples, for screening scarce antibodies produced by primary plasma cells from immunized animals, as well as for selecting clones for recombinant protein production. Additionally, it is contemplated that in addition to its utility for measuring antibody-antigen binding kinetics, the microfluidic bead-based assay described herein can be used for measuring other protein-protein and biomolecular interactions with a wide range of binding affinities, such as protein-carbohydrate binding, protein-DNA (i.e., transcription factor binding) and protein-RNA interactions. It is also contemplated that upon identifying an ASC that secretes antibodies which are optimal for a particular purpose, the ASC in question can be cloned by reverse-transcriptase PCR and standardized cloning techniques.

EXPERIMENTAL METHODS

Microfluidic Device Fabrication and Control

All microfluidic devices were fabricated using multilayer soft lithography (see, for e.g., Unger, M. A. et al. (2000), *Science*, 288: 113-116 and Thorsen, T. et al. (2002), *Science* 298: 580-584. Devices were composed of two layers of poly(dimethylsiloxane) (PDMS) elastomer (GE RTV 615) bonded to No 1.5 glass coverslips (Ted Pella, Inc.). The devices were designed in AutoCAD software (Autodesk) and printed on high resolution (20,000 dpi) transparency masks (CAD/Art Services). Master molds were fabricated in photoresist on silicon wafers (Silicon Quest) by standard optical lithography. The control master molds were fabricated out of 20-25 µm high SU-8 2025 photoresist (Microchem). The flow master molds were fabricated with 12 µm rounded SPR220-7.0 photoresist channels (Rohm and Haas) and 6 µm SU-8 5 photoresist (Microchem) channels with rectangular cross-section. Microfluidic valves were actuated at 30 psi pressure which was controlled using off-chip solenoid valves (Fluidigm Corp) controlled using LabView 7.1 software and a NI-6533 DAQ card (National Instruments). Compressed air (3-4 psi) was used to push reagent solutions into the device.

Reagent Preparation

Protein A-coated 5.5 µm diameter polystyrene beads (Bangs Labs) were incubated with 1 mg/mL solutions of Rabbit anti-mouse polyclonal antibodies (pAbs) (Jackson Immunoresearch). All antibody and antigen solutions were prepared in PBS/BSA/Tween solution consisting of 1×PBS, pH 7.4 (Gibco) with 10 mg/mL BSA (Sigma) and 0.5% Polyoxyethylene (20) sorbitan monolaurate (similar to Tween-20, EMD Biosciences).

Lysozyme from chicken egg white (HEL) was purchased from Sigma, and the D1.3 and HyHEL-5 mouse monoclonal antibodies to lysozyme were generously provided by Dr. Richard Willson (University of Houston). The anti-GFP mouse monoclonal antibody (LGB-1) was purchased from Abcam. Fluorescent protein conjugates were prepared using Dylight488 and Dylight633 NHS esters (Pierce) and were purified using Slide-A-Lyzer dialysis cassettes (Pierce). The concentration of fluorescent conjugates was measured by spectrophotometry (Nanodrop). In order to minimize protein denaturation, fluorescent HEL conjugates were labeled at dye-to-protein (D/P) ratios of less than 1, whereas the D1.3-Dylight488 conjugate was prepared at a D/P ratio of ~5.

Microscopy

The microfluidic devices were imaged on a Nikon TE200 Eclipse inverted epifluorescence microscope equipped with green (470/40 nm excitation, 535/30 nm emission) and red (600/60 nm excitation, 655 nm long-pass emission) fluorescence filter cubes (Chroma Technology). Fluorescence images were taken using a 16-bit, cooled CCD camera (Apogee Alta U2000) and a 100× oil immersion objective (N.A. 1.30, Nikon Plan Fluor). The sensitivity of the fluorescence measurements was tuned by binning pixels on the CCD detection camera and modulating the fluorescence exposure times (20 ms-1 s) with a computer-controlled mechanical shutter (Ludl).

Cell Culture

Mouse D1.3 hybridoma cells were cultured in RPMI 1640 media (Gibco) with 10% FCS. Prior to loading into microfluidic devices, cells were washed by centrifugation at 1500 rpm and re-suspended in fresh media in order to remove antibodies secreted in the cell media.

Microfluidic Bead-Based Fluorescence Assay

A microfluidic device was designed and fabricated to perform bead-based fluorescence measurements of antigen-antibody binding kinetics (see FIGS. 1A and B herein). The device consists of six fluidic inlets, each used for loading a distinct reagent and controlled with an independent control valve, which join into a common fluidic outlet. The fluidic outlet can be partitioned into discrete ~200 pL chambers by actuating a set of microfluidic "sieve" valves which, when actuated, act as filters to immobilize large particles (>1 micron) while still allowing fluid exchange. See, e.g., Marcus, J. S. et al. (2006) *Analytical Chemistry* 78: 3084-3089.

Figure 1C:
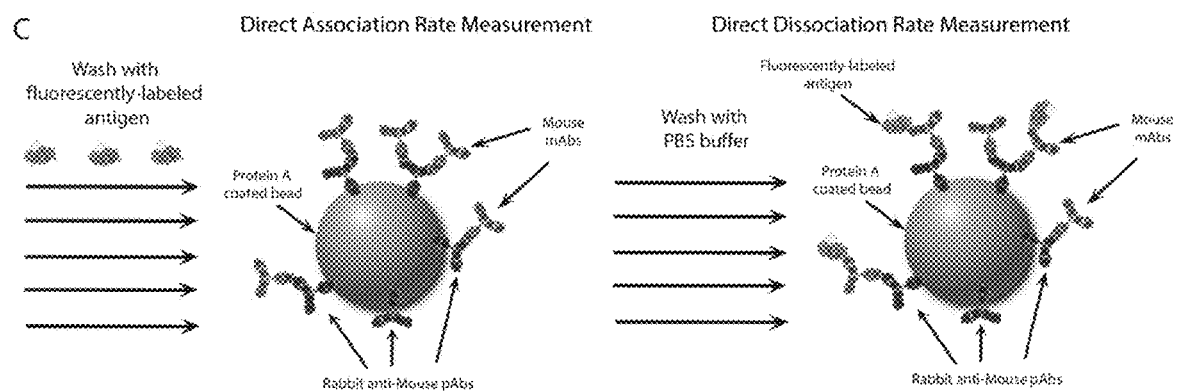

At the start of the experiment, the fluidic outlet was flushed with a PBS/BSA/Tween solution from the top and bottom fluidic inlets in order to pre-coat channel walls and reduce nonspecific binding. Next, 5.5 µm diameter Protein A beads coated with Rabbit anti-mouse pAb were loaded through the device to the fluidic outlet. The microfluidic sieve valves were then actuated and the fluidic outlet was again washed with PBS/BSA/Tween solution to immobilize the beads against the traps and wash out any free rabbit pAb in solution. The beads were then washed with the mouse antibody selected for kinetic characterization. Again, free mouse antibody was washed out of the fluidic outlet using PBS/BSA/Tween. Finally, the beads were washed with fluorescently-labeled antigen and fluorescently imaged at defined time intervals to measure the rate of antibody-antigen association (see FIG. 1C herein). When chemical equilibrium between the antibody and antigen was reached, as detected by a plateau in bead fluorescence, the beads were flushed with PBS buffer and imaged to measure the rate of antibody-antigen dissociation. The process was repeated with varying concentrations of fluorescently-labeled antigen, each loaded onto the microfluidic device from a separate fluidic inlet.

Figure 1D:
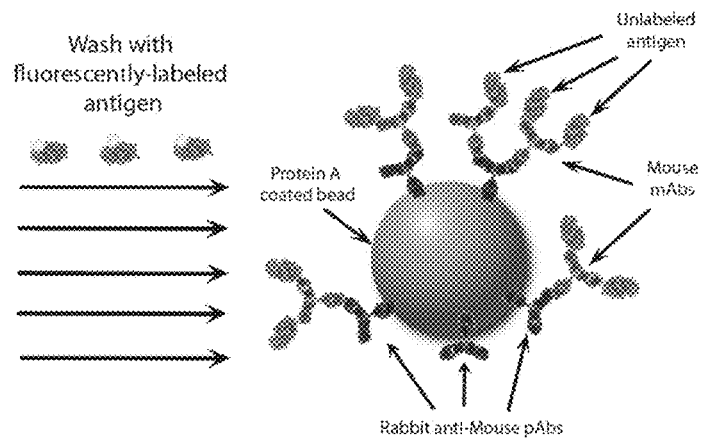
Figure 2A:
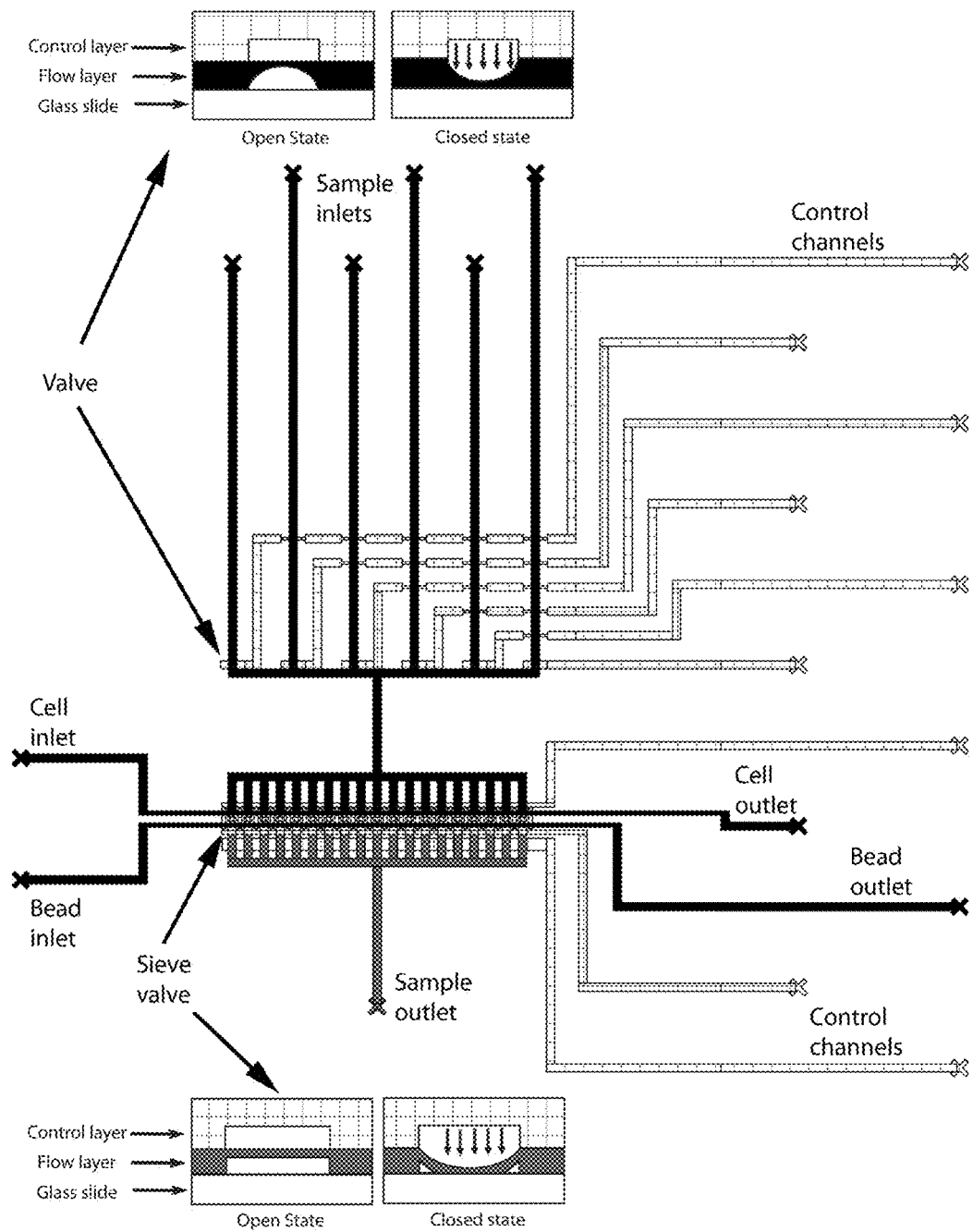
FIGS. 2A-2H show a schematic diagram of an embodiment of a microfluidic device for the detection of antibody secreted from single cells.
Figure 2B:
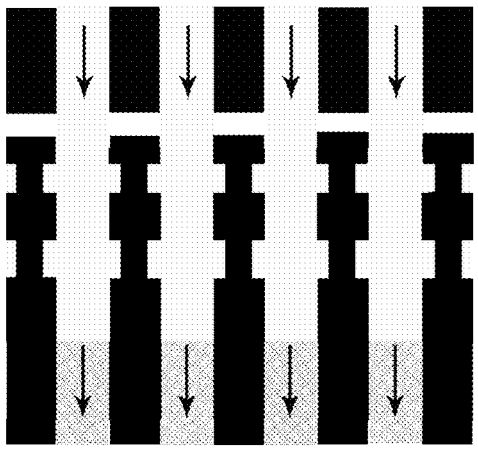
Figure 2C:
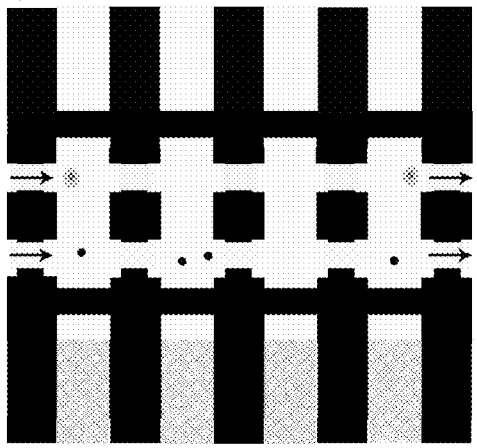
Figure 2D:
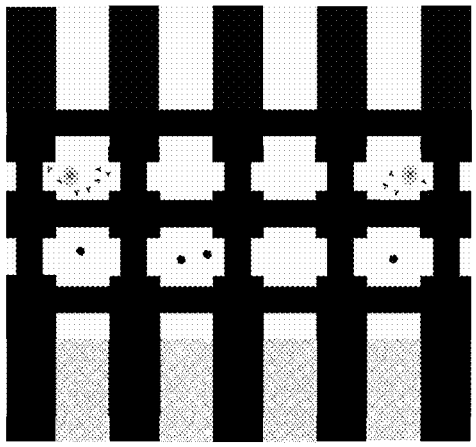
Figure 2E:
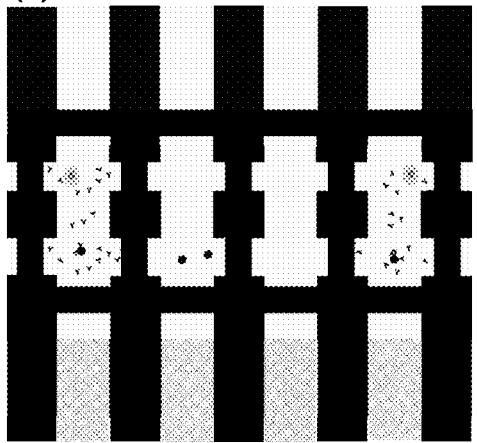
Figure 2F:
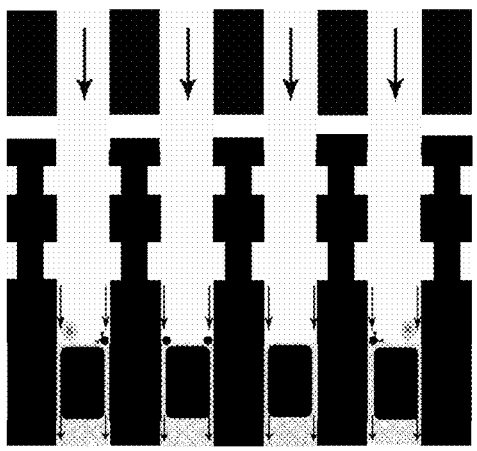
Figure 2G:
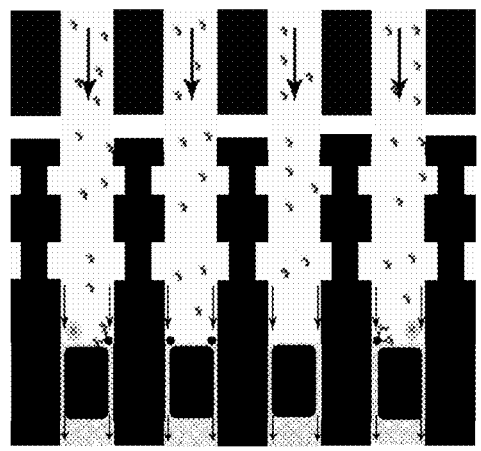
Figure 2H:
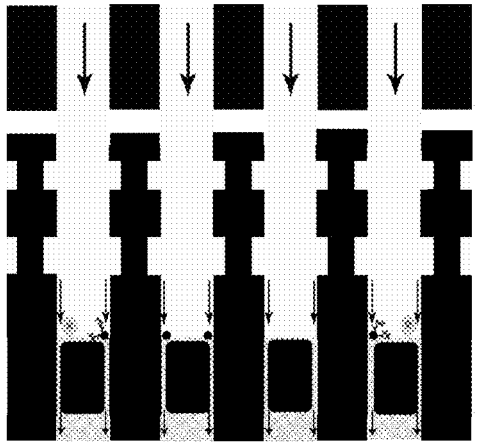

A second version of the microfluidic bead assay was implemented to indirectly measure dissociation kinetics between antibodies and unlabeled antigen molecules by displacement with fluorescently labeled antigen (see FIG. 1D herein). In this assay, after the antibody of interest was captured on Rabbit anti-mouse pAb-coated Protein A beads, beads were washed with unlabeled antigen at high concentration (>1 µM) to saturate all antibody binding sites. Beads were then washed with fluorescently labeled antigen while imaging at defined time intervals. Dissociation of the unlabeled antigen was then inferred by accumulated fluorescence on the beads.

In order to measure the antigen binding kinetics from antibodies secreted from single cells, Protein A beads coated with Rabbit anti-mouse pAb were first immobilized in the fluidic outlet channel using the microfluidic sieve valves. A solution of RPMI-1640 media containing $10^5$ hybridoma cells/mL was then loaded into the device from a separate fluidic inlet and the control valve was momentarily opened to allow for a single hybridoma cell to be brought in close proximity with beads immobilized in the first sieve trap in the fluidic outlet channel. The hybridoma cell was then allowed to incubate next to the beads for 1 hour, and subsequently washed with PBS/BSA/Tween buffer to wash out any free antibody in solution and halt antibody secretion from the cell. Kinetic measurements of antigen binding were then performed in the same manner as with purified antibodies.

FIGS. 2A-2H show a schematic diagram of a microfluidic device operable for detecting antibody secreted from antibody secreting cells. The steps utilized are, for example, as follows: (1) flush microfluidic channels with cell culture media; (2) load channels with antibody secreting cells (top) and capture beads (bottom); (3) incubate cells with beads to capture secreted antibody; (4) trap cells and beads with sieve valves and flush out unbound antibody by blowing buffer over cell-bead mixture; (5) flow fluorescently-labeled antigen over trapped cells and beads; and (6) flush out unbound antigen by blowing buffer over trapped cells and beads and image fluorescent beads.

Data Analysis.

Fluorescent images were analyzed using MaximDL 4 imaging software. Fluorescent intensities were measured by selecting line profiles through the beads and recording the maximum intensity at the bead surface. During protein binding experiments, line profiles were constructed through the same beads at each measurement time point in order to avoid any systemic variations caused by differences in bead-to-bead binding capacity, variation in position in the flow channel and non-uniform illumination over the field of view. The measured fluorescence bead intensities were assumed to be proportional to the concentration of antibody-antigen complex ([AbAg]) and were fit to the following first-order, mass action and Langmuir isotherm equations using nonlinear least squares minimization:

$$F(t) = (F_{max} - F_0)\frac{[Ag]_0}{[Ag]_0 + K_d}\left(1 - e^{-(k_{on}[Ag]_0 + k_{off})t}\right) + F_0 \quad \text{(equation 1)}$$

$$F(t) = (F_{max} - F_0)\frac{[Ag]_0}{[Ag]_0 + K_d}e^{-k_{off}t} + F_0 \quad \text{(equation 2)}$$

$$F(t) = (F_{max} - F_0)\frac{[Ag]_0}{[Ag]_0 + K_d} + F_0 \quad \text{(equation 3)}$$

where F(t) represents the measured bead fluorescence at time t, $F_0$ and $F_{max}$ represent the background and maximum bead fluorescence, respectively, $[Ag]_0$ represents the solution concentration of antigen (in M), and, $k_f$ and $k_r$ represent the intrinsic association and dissociation rate constants, in units of $M^{-1}$ $s^{-1}$ and $s^{-1}$, respectively.

EXAMPLES

The following examples describe embodiments of the invention detailed herein.

Example 1. Measurement of Antibody-Antigen Binding Kinetics on Beads

Figure 3A:
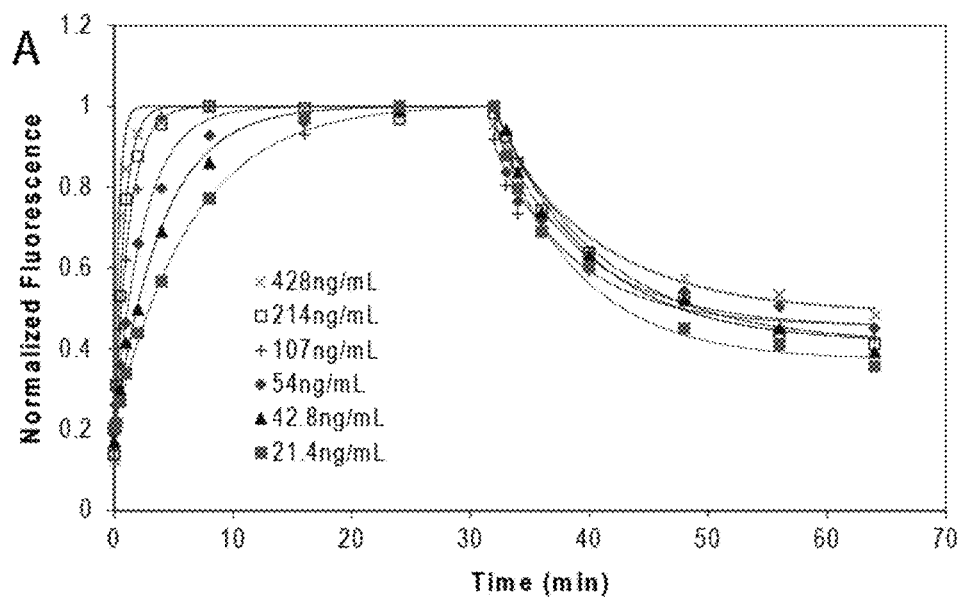
FIGS. 3A-3D show plots of microfluidic bead-based measurements of antibody-antigen binding kinetics. Direct fluorescent measurements of association and dissociation kinetics of FIG. 3A: D1.3 mAb and HEL-Dylight488 conjugate.

The binding kinetics of the D1.3 mouse monoclonal antibody (mAb) to fluorescently-labeled hen egg lysozyme (HEL) was measured using the methodologies and techniques described herein. See: FIG. 3A and Table 1 herein.

TABLE 1

Antibody-antigen binding kinetics measured using the microfluidic fluorescence bead assay.

| Antibody/Antigen interaction | $k_{on}$ ($M^{-1}s^{-1}$) | $k_{off}$ ($s^{-1}$) | $K_d$ |
|---|---|---|---|
| D1.3 mAb/HEL-Dylight488 | $1.87 \pm 0.48 \times 10^6$ | $2.10 \pm 0.25 \times 10^{-3}$ | $1.20 \pm 0.42$ nM |
| D1.3 mAb/HEL-Dylight633 | $1.27 \pm 0.22 \times 10^6$ | $2.15 \pm 0.23 \times 10^{-3}$ | $1.75 \pm 0.46$ nM |
| HyHEL-5 mAb/HEL-Dylight633 | $5.75 \pm 0.71 \times 10^6$ | $1.69 \pm 0.30 \times 10^{-4}$ | $30.0 \pm 7.4$ pM |
| LGB-1 mAb/EGFP | $5.00 \pm 0.72 \times 10^4$ | $5.15 \pm 0.89 \times 10^{-3}$ | $106 \pm 28$ nM |

The measured association and dissociation rate constants for the D1.3/HEL interaction were $1.87\pm0.48\times10^6$ $M^{-1}$ $s^{-1}$ and $2.10\pm0.25\times10^{-3}$ $s^{-1}$, respectively, and were consistent with values of $1.0$-$2.0\times10^6$ $M^{-1}$ $s^{-1}$ and $1.15$-$3.04\times10^{-3}$ $s^{-1}$ previously measured using surface plasmon resonance (SPR) spectroscopy, stopped-flow fluorescence quenching, and competitive ELISA. See, for e.g., Batista, F. D. and Neuberger, M. S. (1998), *Immunity* 8: 751-759 and Ito, W. et al. (1995), *Journal of Molecular Biology* 248: 729-732. A ten-fold smaller association rate constant previously reported for the D1.3/HEL interaction ($1.67\times10^5$ $M$-$s^{-1}$) can likely be attributed to differences between the full D1.3 mAb used in our microfluidic bead-based measurements and the recombinant single-chain antibody fragment used by Bedouelle and coworkers (England et al. (1999) *J Immunol.* 162: 2129-2136).

Figure 3B:
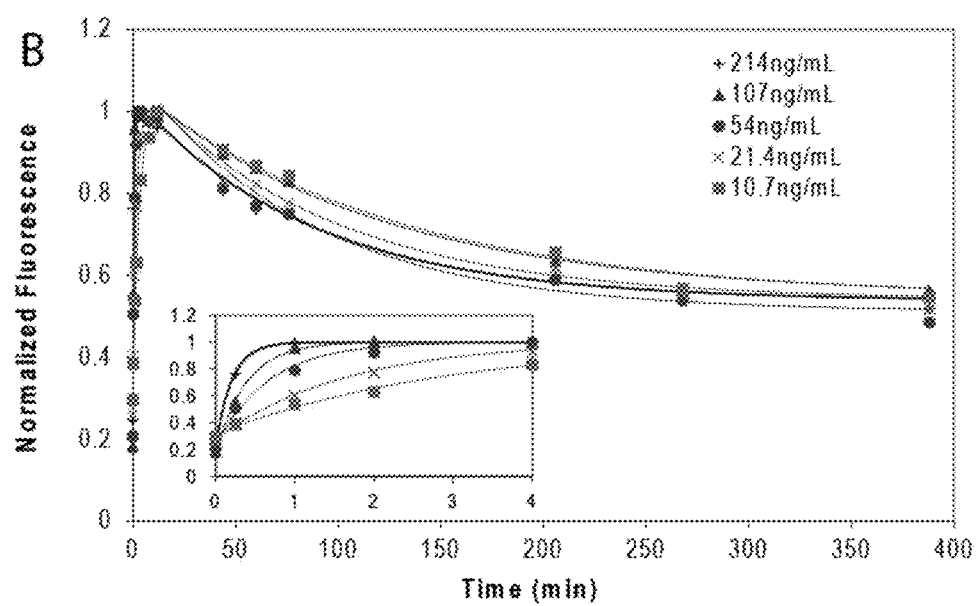
Figure 3C:
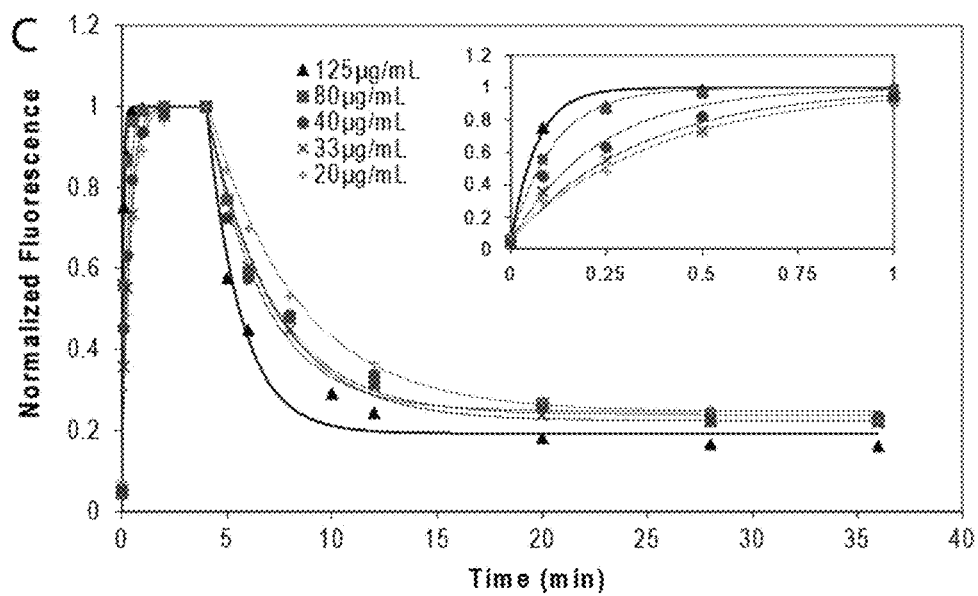
Figure 3D:
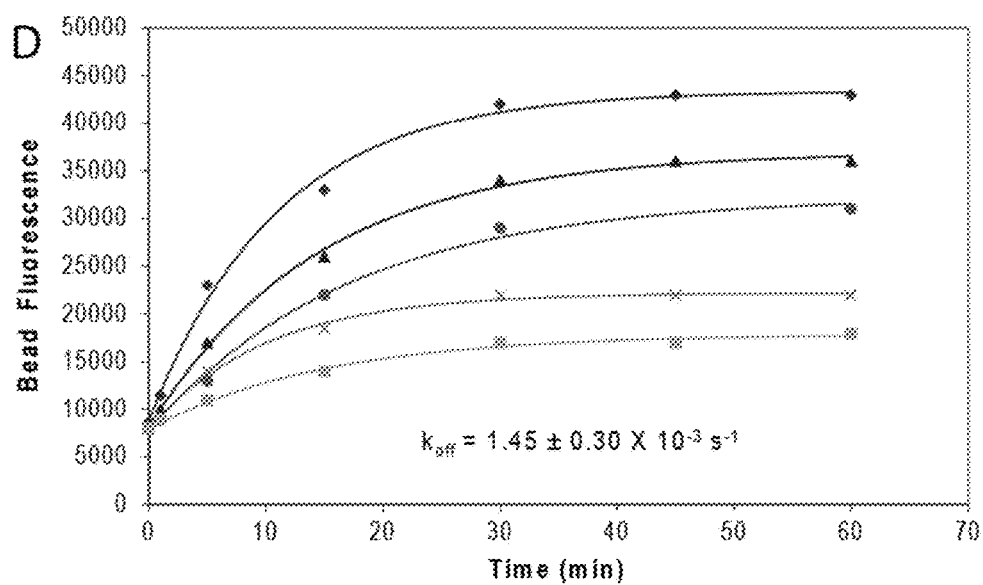

Additionally, indirect, label-free measurements of the D1.3 mAb/HEL dissociation rate constant using a variation of our microfluidic bead assay were performed using the methodologies and techniques described herein. See: FIGS. 1D and 3D herein. In this assay, D1.3 mAbs immobilized on beads were first saturated with unlabeled HEL and subsequently washed with fluorescently-labeled HEL. Measurements of the accumulated bead fluorescence faithfully reflected the D1.3/HEL dissociation kinetics provided the labeled HEL was at a sufficiently high concentration to ensure that dissociation was rate-limiting (i.e. $k_{on}[Ag]>k_{off}$, or, equivalently, $[Ag]>K_d$). Using this method, the dissociation rate constant of D1.3 and unlabeled HEL was measured to be $1.45\pm0.30\times10^{-3}$ $s^{-1}$, in close agreement with direct dissociation measurements between D1.3 and fluorescently-labeled HEL. See Table 1 herein.

The microfluidic bead assay was used to measure the binding kinetics of HEL and HyHEL-5, a distinct mouse mAb with significantly stronger binding affinity to HEL than D1.3. In comparison to the D1.3 mAb, HyHEL-5 bound HEL with a nearly four-fold larger association rate constant ($5.75\pm0.71\times10^6$ $M^{-1}$ $s^{-1}$) and ten-fold smaller dissociation rate constant ($1.69\pm0.30\times10^{-4}$ $s^{-1}$). See: FIG. 3B herein. Thus, HyHEL-5 bound HEL with a ~40-fold smaller equilibrium dissociation constant than D1.3 (30 pM vs. 1.2 nM). See: Table 1 herein. Compared with the microfluidic bead assay, previous measurements of the HyHEL-5/HEL interaction using solution-phase fluorescence anisotropy resulted in a similar dissociation rate constant ($2.2\times10^{-4}$ $s^{-1}$), but a three- to five-fold larger association rate constant ($1.5$-$3.3\times10^7$ $M^{-1}$ $s^{-1}$). See, for e.g., Xavier, K. A. and Willson, R. C. (1998) *Biophys. J.* 74: 2036-2045. Since HyHEL-5 mAb binds HEL with near diffusion-limited association kinetics, immobilization of the mAb in the microfluidic bead assay could potentially result in slower association kinetics when compared with solution-phase fluorescence anisotropy measurements. However, since the diffusion constant of HEL is approximately three times larger than that of the mAb, immobilization of the HyHEL-5 mAb would reduce the effective diffusion coefficient ($D\pm D_{mAb}+D_{HEL}$) and, hence, the apparent association rate constant by at most 25%. See, for e.g., Tyn, M. T. and Gusek, T. W. (1990), *Biotechnology and Bioengineering* 35: 327-338 and He, L. and Niemeyer, B. (2003), *Biotechnol. Prog.* 2003, 19: 544-548. Therefore, the difference in measured and reported association rate constants is likely a result of different buffer solutions, as the HyHEL-5 and HEL binding interaction is known to be very sensitive to solution pH and buffer salt concentration. See, for e.g., Xavier, K. A. and Willson, R. C. (1998) *Biophys. J.* 74: 2036-2045 and Dlugosz et al. (2009), *The Journal of Physical Chemistry* 113: 15662-15669.

The binding kinetics of a commercially available mouse monoclonal antibody (LGB-1, Abcam) to enhanced green fluorescent protein (eGFP) were also measured using the methodologies and techniques described herein. See: FIGS. 3A-3D herein. This binding interaction was chosen to demonstrate that the bead-based assay can be used to measure binding kinetics of a previously uncharacterized antibody without optimizing the bead immobilization chemistry. In this instance, native eGFP fluorescence was measured without an exogenous fluorescent label. The measured association and dissociation rate constants for the LGB-1/eGFP interaction were $5.00\pm0.72\times10^4$ $M^{-1}$ $s^{-1}$ and $5.15\pm0.89\times10^{-3}$ $s^{-1}$, respectively. See: Table 1 herein.

Collectively, the measured binding kinetics of the anti-lysozyme and anti-eGFP mAbs span nearly four orders of magnitude in equilibrium dissociation constants (30 pM-100 nM), with association rate constants varying from $5\times10^4$-$10^6$ $M^{-1}$ $s^{-1}$ and dissociation rate constants ranging from $10^{-3}$-$10^4$ $s^{-1}$. See: Table 1 herein. In principle, the microfluidic bead-based assay can be used to characterize stronger antibody-antigen interactions than the HyHEL-5/HEL interaction; however, binding interactions with dissociation rate constants lower than $10^{-4}$ $s^{-1}$ require measurements to be taken over several days or weeks. On the other hand, the bead-based assay can be readily used to measure binding interactions weaker than the LGB-1/eGFP interaction. Using this assay, the practical upper limit in measurable dissociation rate constants is approximately $10^{-1}$ $s^{-1}$, as a result of the time required to exchange solutions in the microfluidic device. Thus, the microfluidic bead-based assay should enable characterization of antibody-antigen interactions that span greater than six orders of magnitude in equilibrium binding affinity.

Figure 4A:
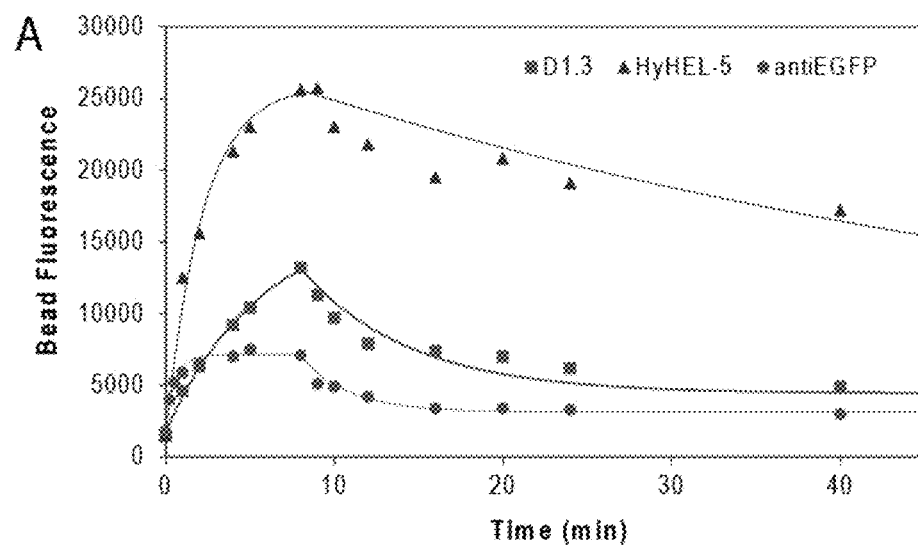
FIGS. 4A-4B show simultaneous measurement of multiple antibody-antigen binding kinetics using optical and spatial multiplexing.
Figure 4B:
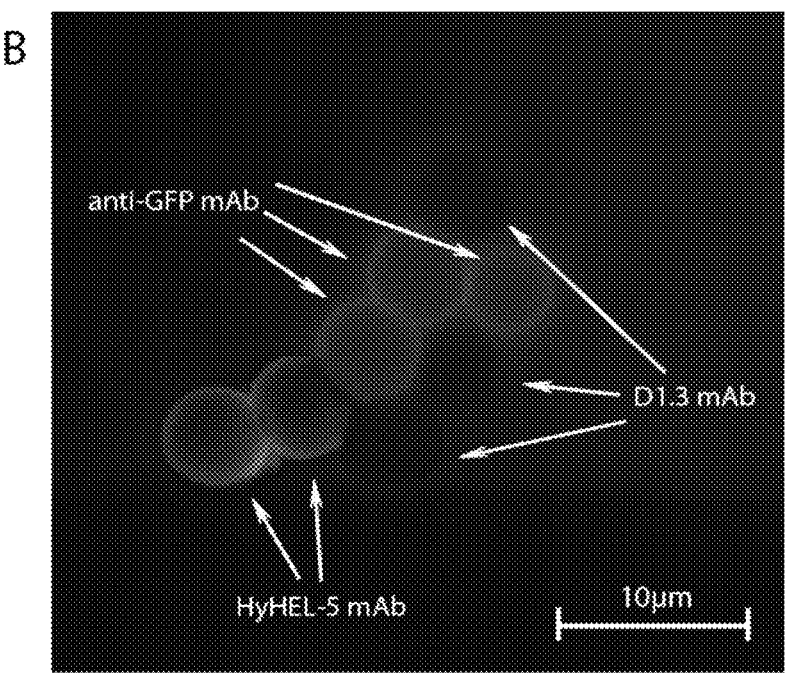

Example 2. Simultaneous Measurement of Multiple Antibody-Antigen Binding Kinetics Using Optical and Spatial Multiplexing The binding kinetics of multiple antibody-antigen interactions were measured simultaneously using both optical and spatial multiplexing of the bead-based assay using the methodologies and techniques described herein. Each antibody was immobilized on a distinct population of beads and, subsequently, beads from each population were sequentially trapped using sieve valves on the microfluidic device. Since beads trapped by the sieve valves remain immobilized throughout the duration of each experiment, the spatial address of beads was tracked in order to identify each antibody. Subsequently, the trapped beads were washed with a mixture of antigens, each labeled with a spectrally distinct fluorophore. The beads were then imaged with different fluorescence filter sets designed to coincide with each fluorescent antigen. In this manner, the binding kinetics of 3 different monoclonal antibodies (D1.3, HyHEL-5 and LGB-1) to two different fluorescent antigens (HEL-Dylight488 and eGFP) were simultaneously measured. See: FIGS. 4A-4B herein. By employing this strategy, it was possible to spectrally distinguish which beads were coated with anti-lysozyme mAbs or anti-eGFP mAbs, whereas the two anti-lysozyme mAbs (D1.3 and HyHEL-5) were discriminated based on their unique binding kinetics for HEL. In addition, the fluorescence intensities of HyHEL-5 coated beads were significantly higher than the D1.3 coated beads, consistent with the fact that HyHEL-5 binds HEL with a significantly lower equilibrium dissociation constant than D1.3. See: FIGS. 4A-4B herein. This technique can be extended to measure any combination of m×n antibody-antigen interactions in which m antibodies are immobilized on different beads and exposed to a solution of n antigens, each with a spectrally-resolvable fluorescent label. In practice, several hundred antibody-antigen interactions could be measured simultaneously by imaging up to 100 beads in a single field of view with five to six spectrally distinct fluorophores. Multiplexed bead measurements could be used for simultaneously analyzing the binding kinetics and binding specificities of a panel of mAbs to multiple different antigens in serum and other complex mixtures.

Figure 7A:
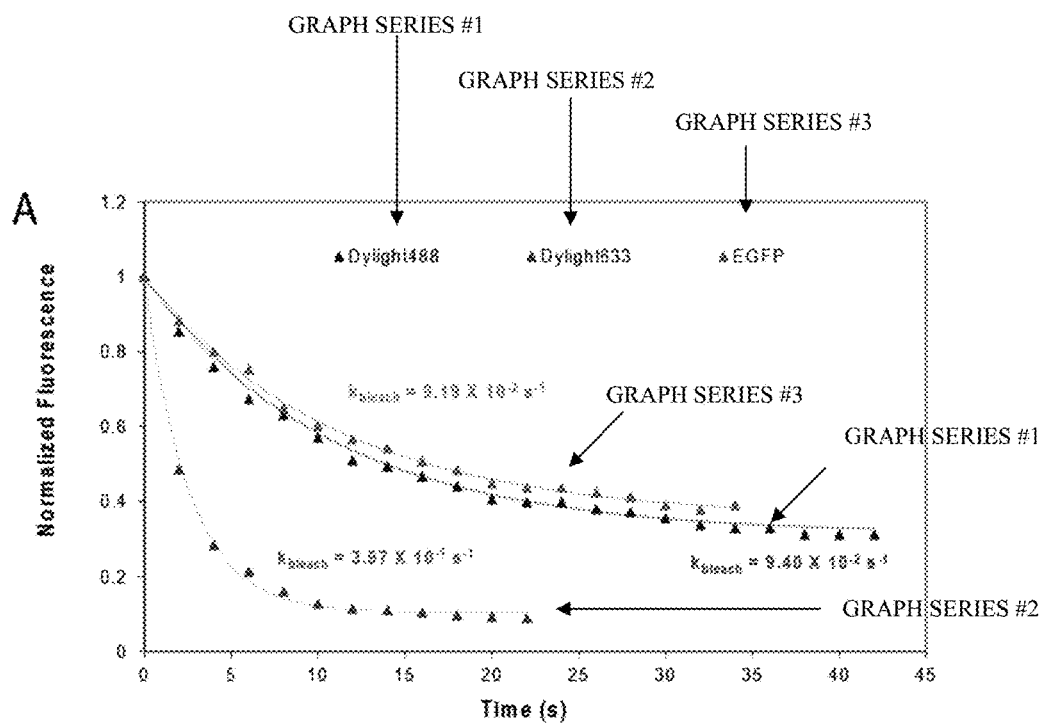
FIGS. 7A-7B show the effect of fluorophore stability on measured antibody-antigen binding kinetics.
Figure 7B:
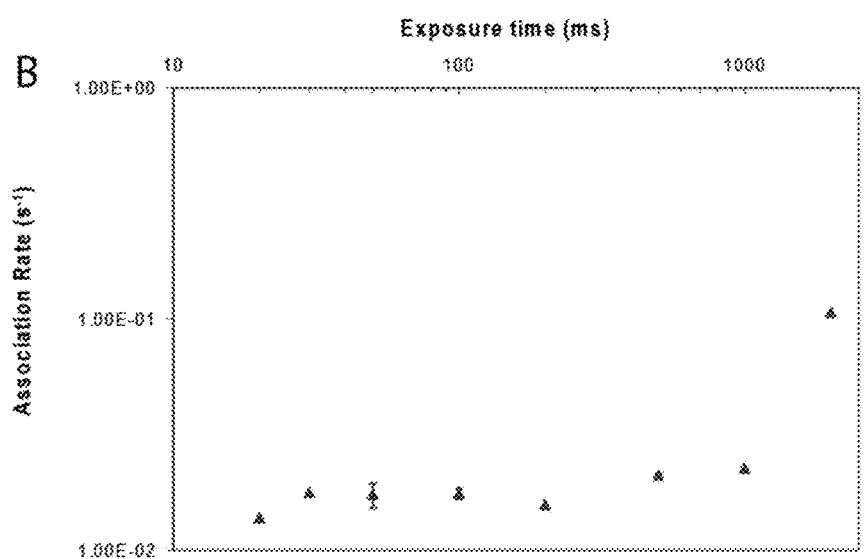

Example 3. Microfluidic Bead-Based Fluorescence Measurements Reflect Intrinsic Antibody-Antigen Binding Kinetics A series of experiments were performed using the methodologies and techniques described herein to verify that bead-based fluorescence measurements reflected intrinsic antibody-antigen binding kinetics, and were unaffected by artifacts arising from fluorescent labeling of the antigen, antibody immobilization, diffusion limitation or mass transport effects. Fluorescent labeling of HEL did not alter the intrinsic D1.3/HEL binding kinetics, as indicated by the agreement between microfluidic bead-based measurements using fluorescently labeled HEL and previously reported measurements using SPR spectroscopy with unlabeled HEL. See, for e.g., Batista, F. D. and Neuberger, M. S. (1998), *Immunity* 8: 751-759 and Ito, W. et al. (1995), *Journal of Molecular Biology* 248: 729-732. Moreover, no differences were observed in bead-based kinetic measurements of the D1.3 mAb binding to HEL labeled with two different fluorophores, Dylight488 and Dylight633 (Pierce). See: Table 1 herein. It was ensured that photobleaching of fluorophores did not affect the measured binding kinetics by measuring the photobleaching rates of the of the fluorescent dyes used in this study (Dylight488, Dylight633, and eGFP) and selecting fluorescence exposure times of less than 100 ms, such that each measurement resulted in less than 5% reduction in bead fluorescence. See: FIG. 7A herein. Indeed, measured binding kinetics were consistent over a large range of fluorescence exposure times (ms), whereas exposure times of greater than is resulted in substantial photobleaching and an artificial increase in measured association and dissociation binding kinetics when compared to intrinsic kinetics. See FIG. 7B herein.

Figure 8:
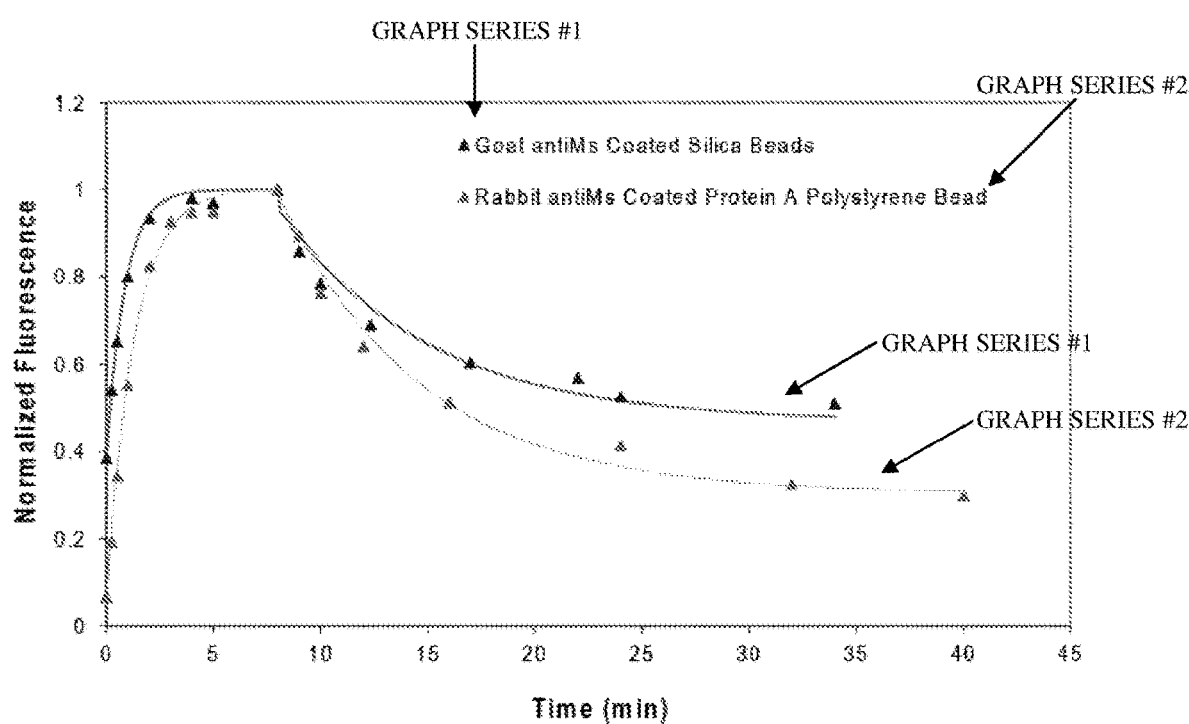
FIG. 8 shows the effect of different bead immobilization chemistries on measured antibody-antigen binding kinetics. Measured kinetics are unaffected by bead composition (silica or polystyrene) or by different polyclonal capture antibodies (rabbit or goat pAbs).
Figure 9:
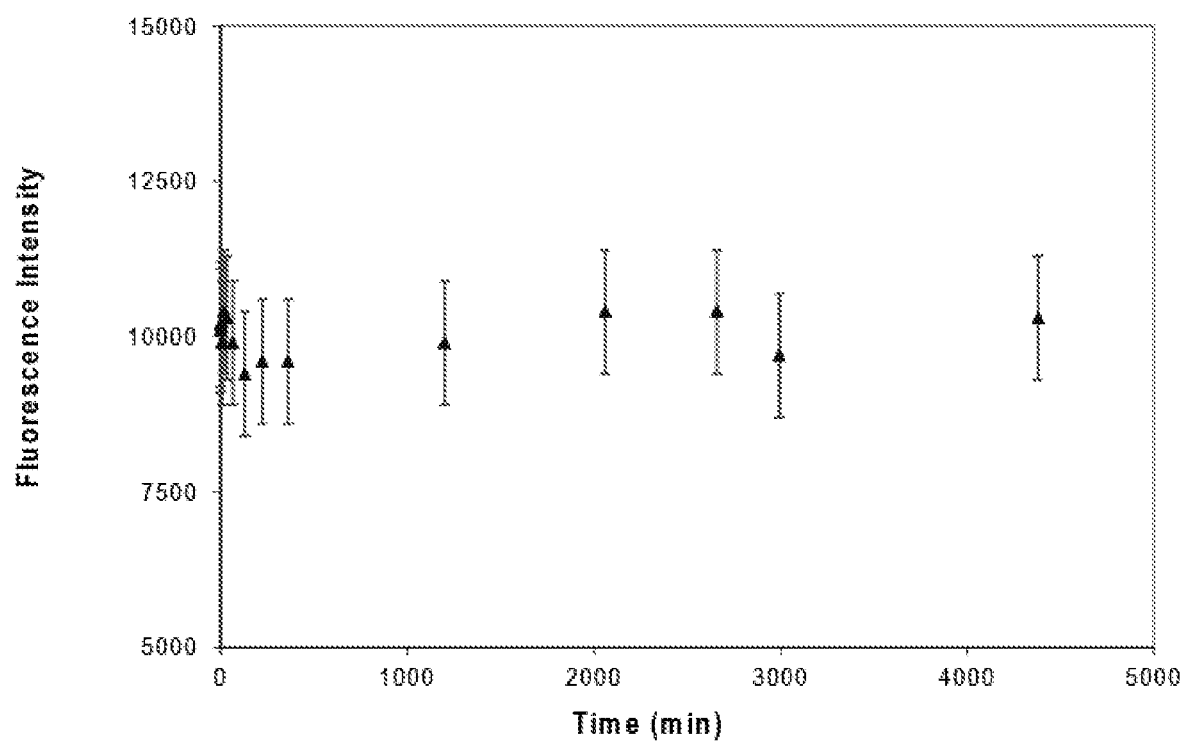
FIG. 9 shows a plot of measured dissociation kinetics of mouse mAb from antibody capture beads. No dissociation of D1.3 mAb-Dylight488 conjugate from Rabbit anti-Ms pAb coated beads was observed over 3 days.

To examine the effect of different antibody bead immobilization chemistries, we verified that measured association and dissociation rate constants for the D1.3/HEL interaction were the same when captured on silica or polystyrene beads coated with either rabbit or goat anti-mouse polyclonal antibody. See: FIG. 8 herein. It was further verified that multivalent binding between the rabbit anti-mouse pAbs and fluorescently-labeled D1.3 mAb resulted in no detectable dissociation over the course of 3 days, which would otherwise artificially accelerate the measured antibody-antigen binding kinetics. See: FIG. 9 herein. The nearly irreversible bond between rabbit pAb and the mouse mAbs was critical to successful antibody-antigen binding kinetic measurements as attempts to measure D1.3/HEL binding kinetics using Protein A beads without Rabbit anti-mouse pAbs were unsuccessful due to rapid dissociation (and low affinity) of protein A/mouse mAb complexes.

Figure 10:
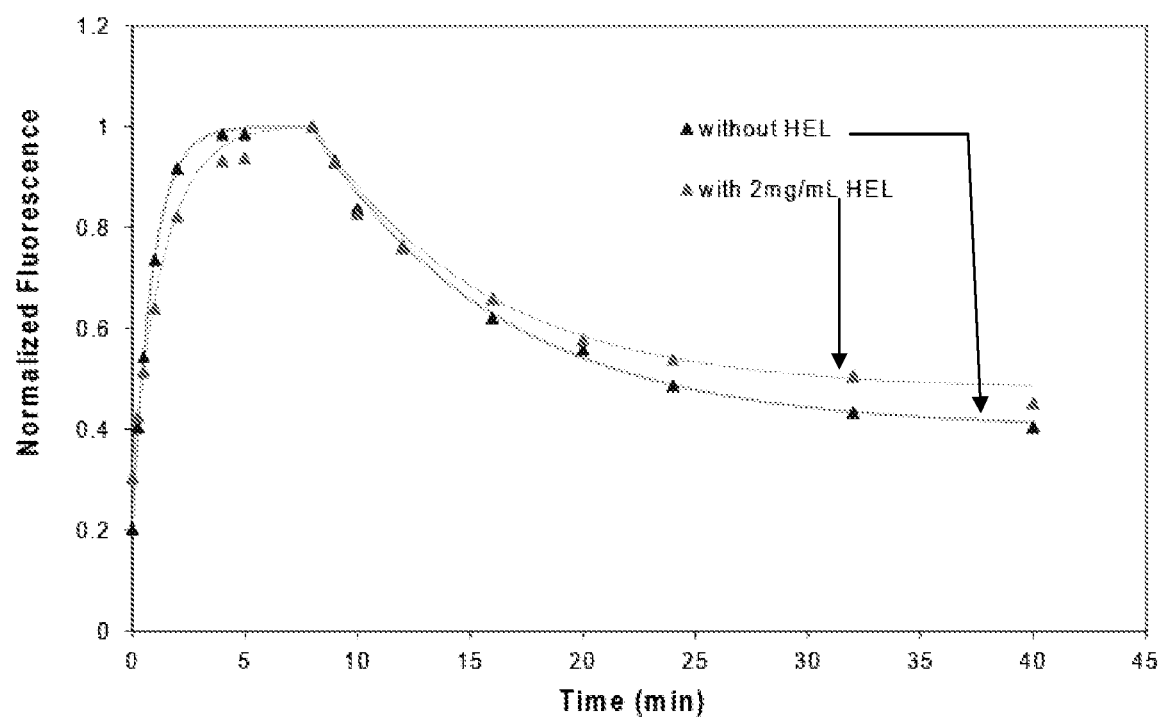
FIG. 10 shows a plot of the effect of antigen re-binding on measured antibody-antigen dissociation kinetics. Dissociation kinetics of D1.3 mAb and HEL-Dylight488 conjugate were unaffected by the presence of a large concentration of competitive antigen (2 mg/mL HEL).
Figure 11:
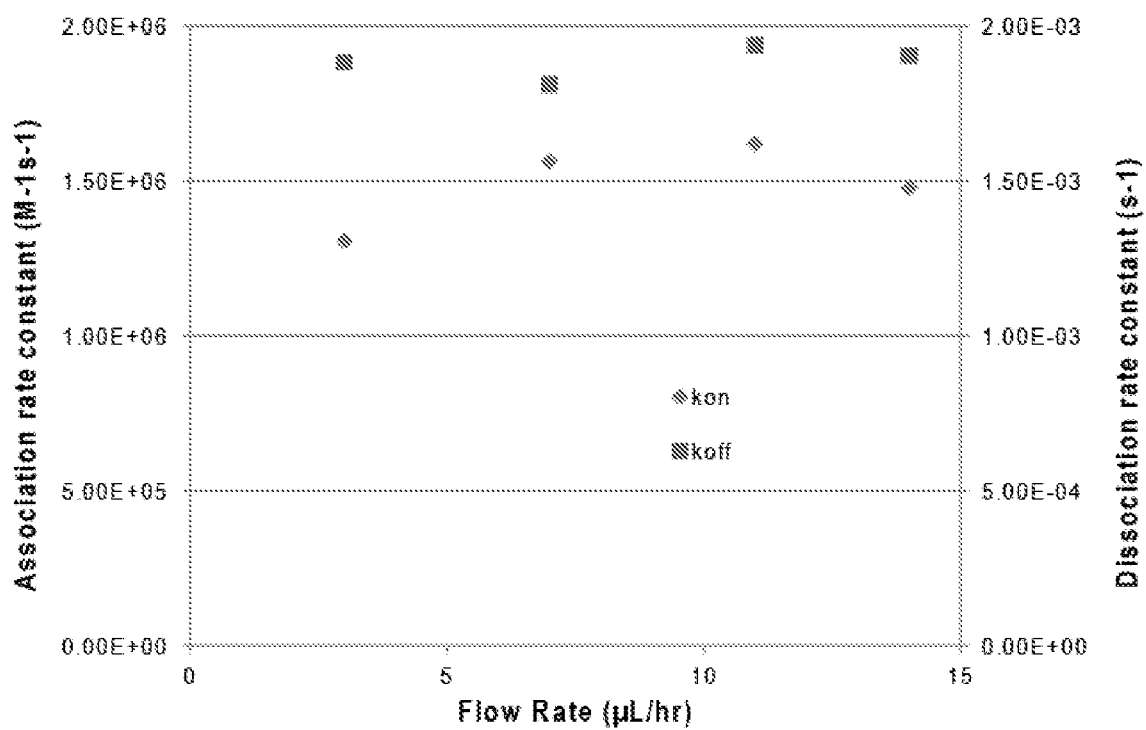
FIG. 11 shows a plot of the effect of mass transport on measured antibody-antigen binding kinetics. Association and dissociation kinetics of D1.3 mAb and HEL-Dylight488 conjugate were unaffected by varying flow rates over a range of ~3-15 µL/hr.
Figures 13A, 13B:
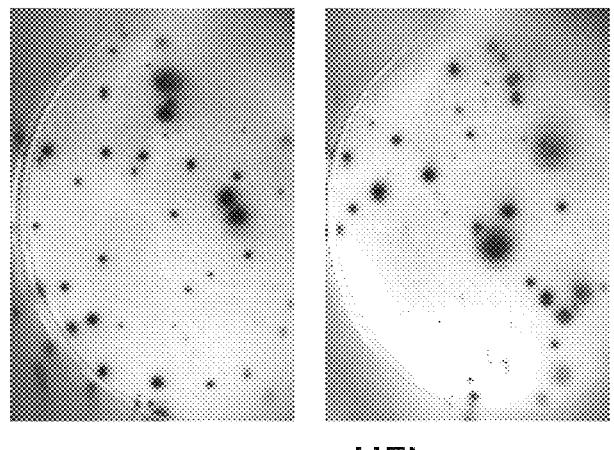
FIGS. 13A-13B show an image of an ELISPOT control assay confirming that the cells depicted in FIGS. 12A-12C are ASCs.

Several experiments were also conducted to verify that diffusion limitation and mass transport did not affect bead-based measurements of antibody-antigen binding kinetics. In the diffusion-limited regime, antibodies adjacent on the bead surface would compete for fluorescent antigen, thus reducing the apparent association rate constant. Similarly, the apparent rate of antibody-antigen dissociation would be reduced due to antigen rebinding to adjacent antibodies. See, for e.g., Berg, H. C. and Purcell, E. M. (1977), *Biophys. J.* 20: 193-219 and Lauffenburger, D. A. and Linderman, J. (1965) Receptors: Models for Binding, *Trafficking, and Signaling*; Oxford University Press. Nearly identical association and dissociation kinetics for the D1.3-HEL interaction was measured by varying the amount of bead-immobilized D1.3 mAb over two orders of magnitude. See FIG. 10 herein. Dissociation kinetics of the D1.3 antibody and fluorescently labeled HEL were also similar both in the presence and absence of a high concentration (~2 mg/mL) of competitive unlabeled HEL antigen. See: FIG. 10 herein. Thus, there was no observable competition between antibodies adjacent to one another on the beads and, hence, no diffusion limitation. It was also confirmed that the association and dissociation rate constants of the D1.3-HEL interaction remained constant over a range of flow rates from 3-15 µL/hr, suggesting no effect of mass transport on the measured kinetics. See FIG. 11 herein.

Figure 5A:
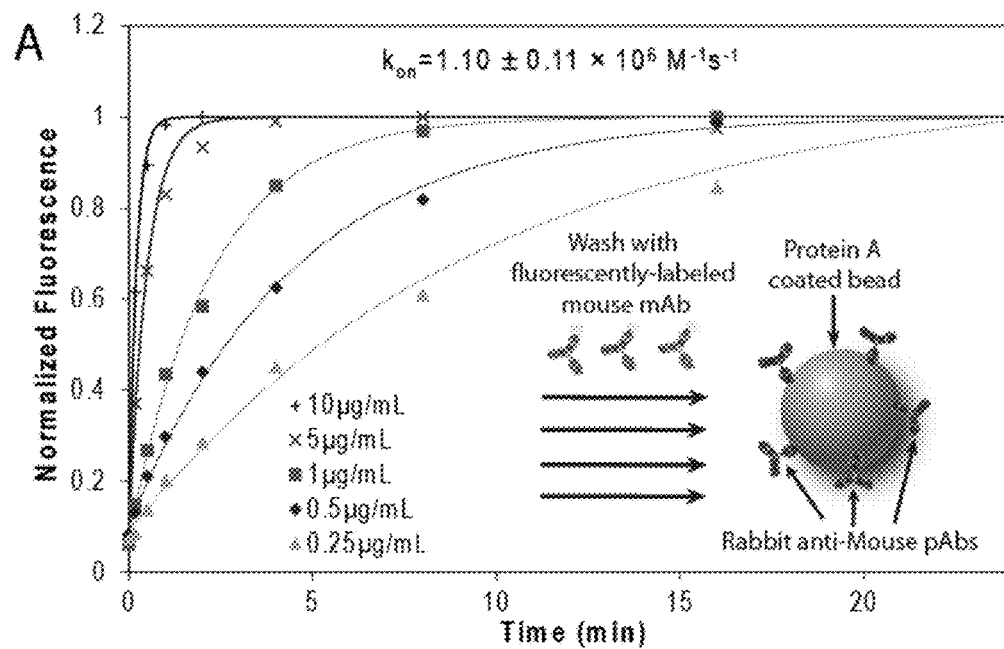
FIGS. 5A-5D show plots of sensitivity and detection limit of antibody-antigen binding kinetics measurements.
Figure 5B:
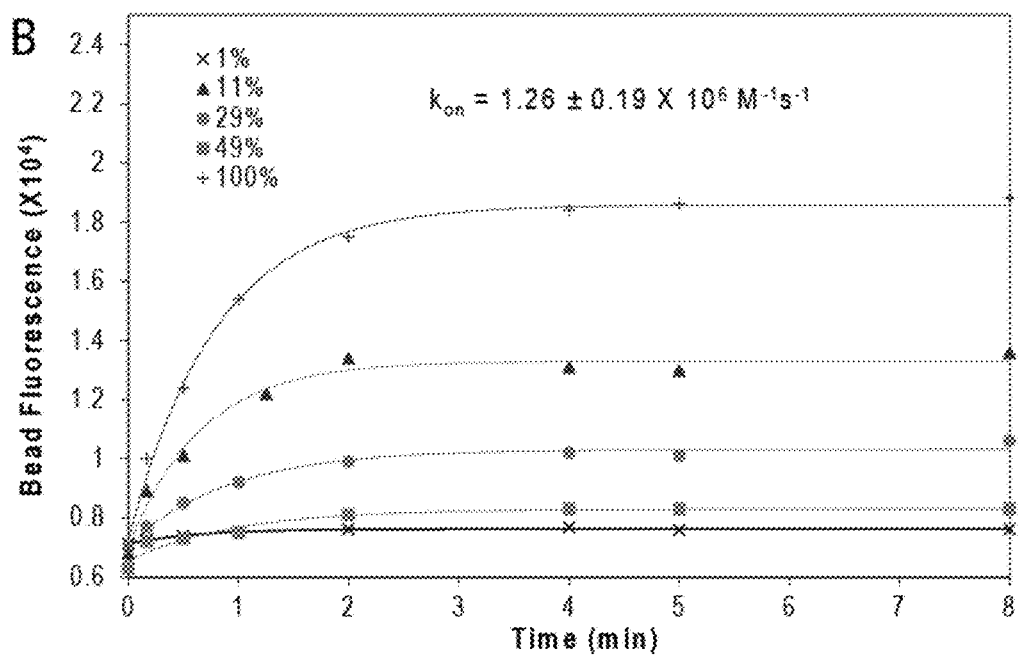
Figure 5C:
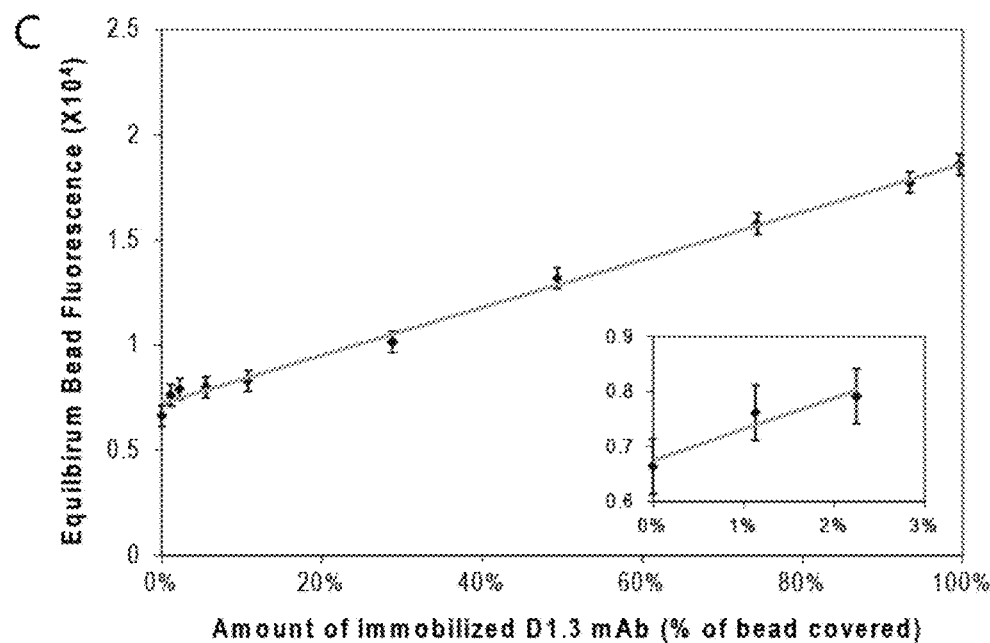
Figure 5D:
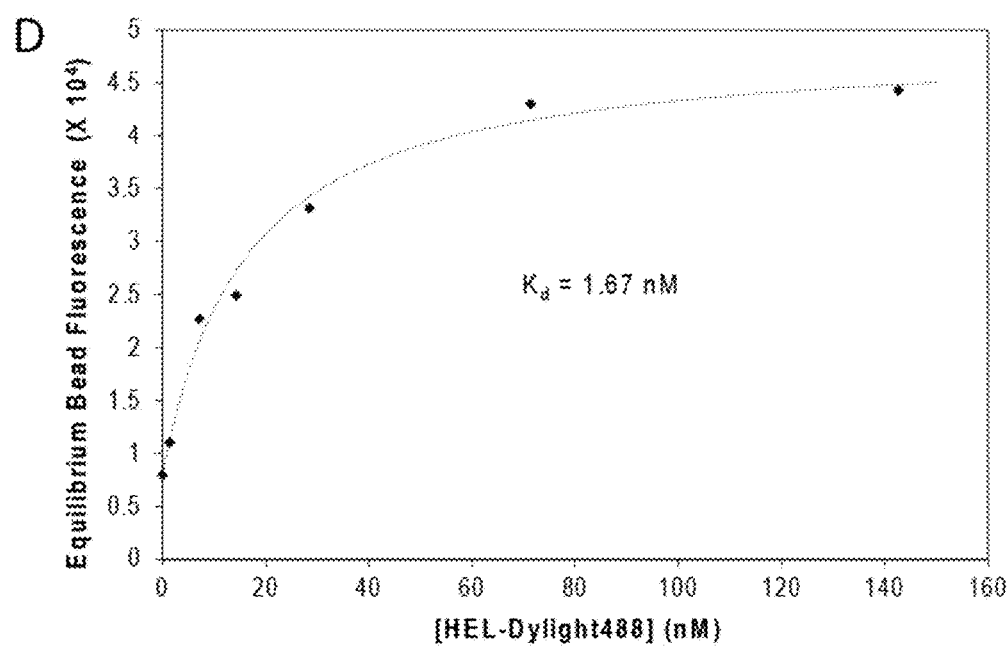

Example 4. Bead-Based Kinetic Measurements Exhibit Low Detection Limits and Minimal Sample Consumption To quantify the detection limit and minimal sample consumption required for microfluidic bead-based measurements of antibody-antigen binding kinetics, antibody-antigen binding kinetics were measured using varying amounts of bead-immobilized mAb along with the methodologies and techniques described herein. The association rate constant of fluorescently-labeled D1.3 mAb binding to Rabbit anti-mouse pAb coated Protein A beads was measured. See: FIG. 5A herein. Using the measured kinetic on-rate constant for this interaction ($k_{on}$=1.10±0.11×10$^6$ M$^{-1}$ s$^{-1}$) and modulating the loading time of D1.3 mAb, the amount of bead-immobilized D1.3 mAb was varied over two orders of magnitude. Then, the antibody-antigen binding kinetics with as little as 1% of the bead surface covered with D1.3 mAb was successfully measured. See: FIG. 5B herein. Using the manufacturer's specifications as well as steric considerations, a single 5.5 micron bead can bind 4×10$^6$ antibody molecules (~6.6 amol); therefore, it was estimated that the detection limit of our microfluidic fluorescence bead assay is to be ~4×10$^4$ antibodies or ~66 zeptomoles. See: FIG. 5C herein. In contrast, SPR spectroscopy requires at least 200 pg (~10$^9$ molecules) of immobilized antibody in order to generate a detectable refractive index change. See, for e.g., Biacore Life Sciences—Biacore 3000 System Information. World-wide-web site: biacore.com/lifesciences/products/systems_overview/3000/system_information/index.html.

Additionally, D1.3/HEL binding kinetics were successfully measured by loading less than 2 million D1.3 mAb molecules (~3 attomoles) into the microfluidic device. In theory, the minimum sample consumption of the microfluidic bead assay could be reduced even further by reducing losses associated with channel dead volumes and optimizing the capture efficiency of antibodies on beads, as well as using microfluidic pumps to achieve flow rates less than 1 µL/hr. Thus, when compared with alternative techniques and SPR spectroscopy, our microfluidic bead-based assay can measure antigen-antibody binding kinetics with a reduction in both detection limit and sample consumption by four orders of magnitude.

Figure 6A:
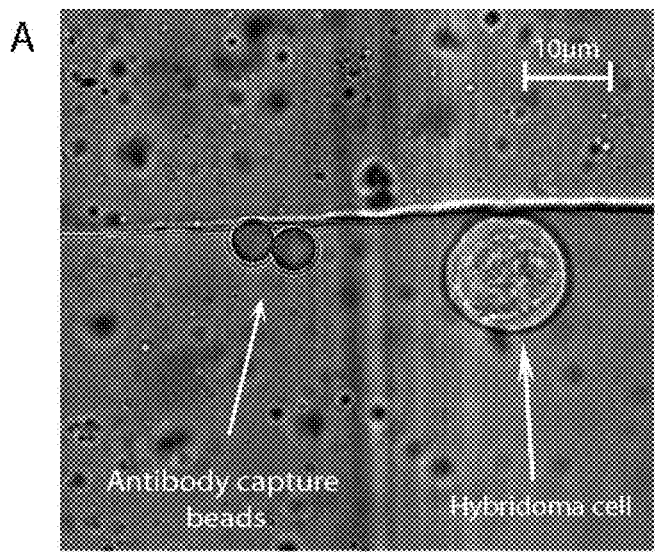
FIGS. 6A-6B show antibody-antigen binding kinetics measured using antibodies secreted from a single cell.
Figure 6B:
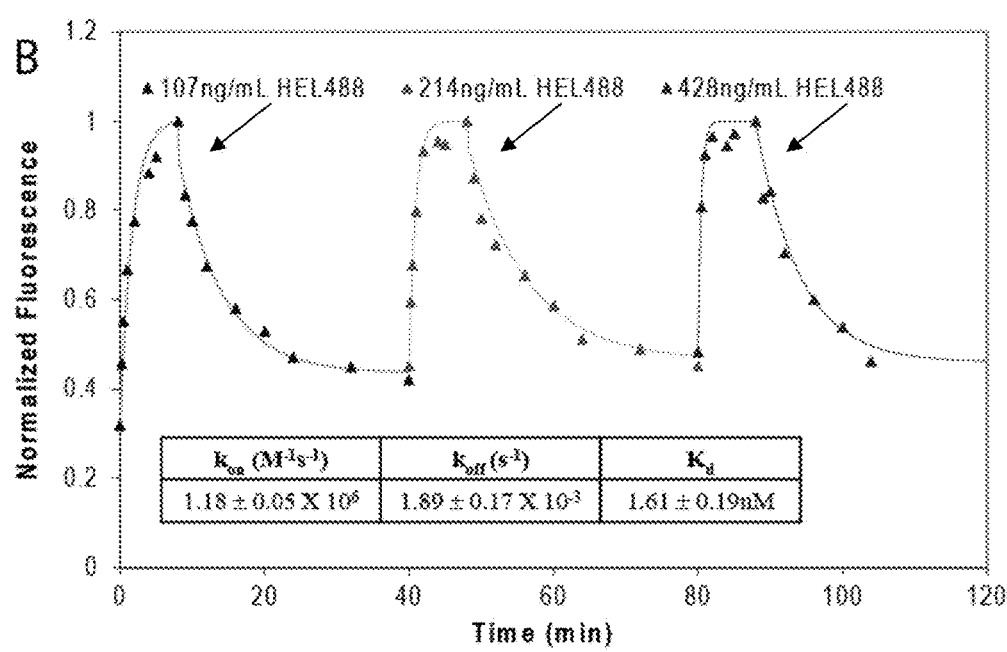

Example 5. Measurement of Binding Kinetics of Antigen and Antibody Secreted from Single Cells Based on the low detection limit of the bead-based assay and in an effort to measure the antigen binding kinetics of antibodies secreted from single antibody secreting cells, single D1.3 hybridoma cells were loaded adjacent to Rabbit anti-Mouse pAb coated Protein A beads captured in the microfluidic device, and then co-incubated the cells and beads for 1 hour at room temperature. See: FIGS. 6A-6B herein. Subsequently, antibody-antigen binding kinetics were measured by recording the fluorescence of a single bead washed with buffer and successively higher concentrations of fluorescent antigen, in a manner analogous to the single-cycle kinetics technique used with SPR spectroscopy. See, for e.g., Biacore Life Sciences—Single-Cycle Kinetics. World-wide-website: biacore.com/lifesciences/technology/introduction/data_interaction/SCK/index.html and Abdiche et al. (2008) *Analytical Biochemistry* 377: 209-217. Using the methodologies and experimental techniques described herein, the association and dissociation rate constants for the D1.3/HEL interaction were successfully measured using antibodies secreted by a single D1.3 hybridoma cell, which were consistent with measurements on purified antibodies. See: FIGS. 6A-6B and Table 1 herein.

Antibody-secreting cells are known to secrete thousands of antibodies per second at 37° C., and would, therefore, secrete enough antibodies in approximately one hour to saturate the surface of a single 5.5 µm bead with maximum binding capacity of ~4×10$^6$ antibody molecules. See, for e.g., Niels Jerne (1984) The Generative Grammar of the Immune System and McKinney et al. (1995) *Journal of Biotechnology* 40: 31-48. While it is reasonable to suspect that the hybridoma cells secrete antibodies at a reduced rate when incubated at room temperature; nonetheless, single D1.3 hybridoma cells secreted sufficient antibody within 1 hour at room temperature for complete kinetic characterization. However, based on the incubation time and detection limit of the assay (~4×10$^4$ antibodies), it can be inferred that single hybridoma cells secreted greater than 10 antibodies/second when incubated at room temperature in the microfluidic device.

Examples 1-5 show that the methods described herein are suitable for measuring antibody-antigen kinetics in a microfluidic environment from a single cell.

Example 6. Dual Function Beads

Figure 14:
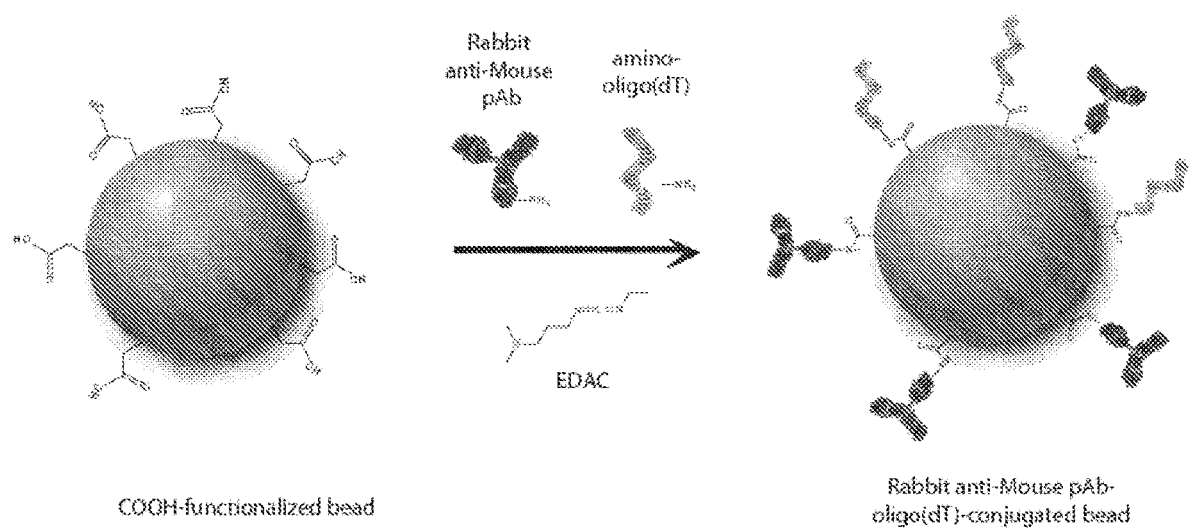
FIG. 14 shows a scheme for preparing dual-capture (i.e., dual-function) beads using carbodiimide chemistry.
Figure 15A:
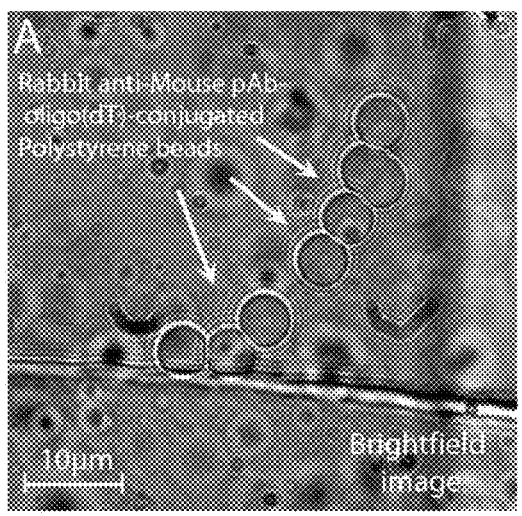
FIGS. 15A-15C show images of dual-function beads. Polystyrene COOH beads were conjugated with rabbit anti-mouse pAb and amine functionalized oligo(dT)$_{25}$ using carbodiimide chemistry.
Figure 15B:
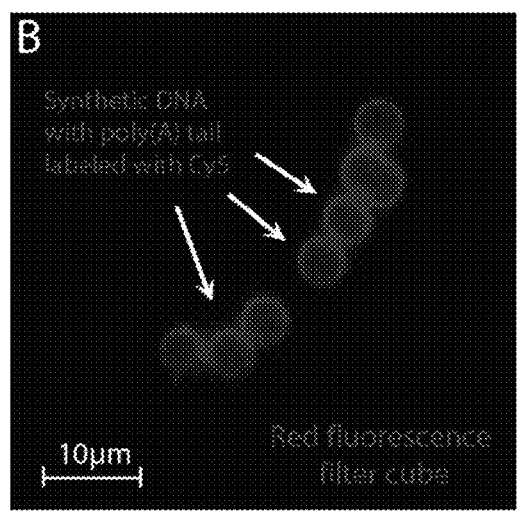
Figure 15C:
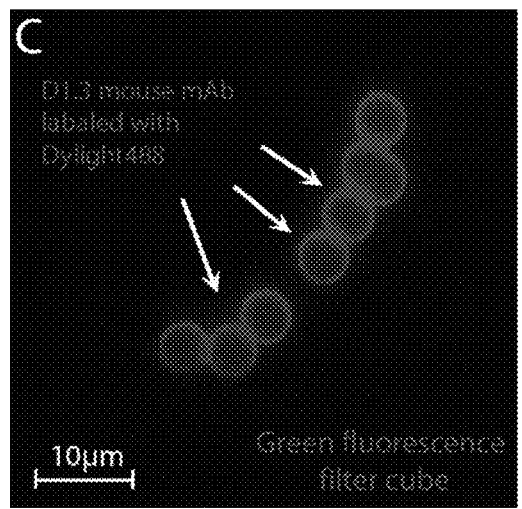

An overview of a scheme for preparing dual-capture (i.e., dual function) beads using carbodiimide chemistry is shown in FIG. 14. A representative experiment utilizing dual function beads is shown in FIGS. 15A-15C. Briefly, polystyrene COOH beads (Bangs Labs) were conjugated with Rabbit anti-mouse pAb (Jackson ImmunoResearch) and amine-functionalized oligo(dT)$_{25}$ (Genelink) using carbodiimide chemistry. In FIG. 15A, a brightfield image of dual-function beads trapped using a microfluidic sieve valve is shown. In FIG. 15B, a fluorescence image of synthetic single-stranded DNA molecules captured on dual-function beads is shown. Synthetic DNA molecules are labeled with Cy5 fluorophore for visualization and also contain a poly(A) tail that binds to the oligo(dT) on the bead surface. In FIG. 15C, a fluorescence image of mouse D1.3 monoclonal antibody (mAb) captured on dual-function beads. D1.3 mAbs are labeled with Dylight488 fluorophore for visualization and bind to the Rabbit anti-Mouse pAb on the bead surface.

It will be understood that while carboxylic acid (COOH) beads are disclosed herein, other beads, which make use of alternate chemical interactions, could also be used, See: for e.g., G. T. Hermanson (2008), *Bioconjugate Techniques*, 2nd Edition, Published by Academic Press, Inc. For example, an alternate scheme for preparing thee beads would be to use streptavidin coated beads and to mix these beads with biotinylized rabbit anti-mouse pAbs and biotinylated oligo (dT).

Example 7. Multiplex RT-PCR of the Antibody Heavy and Light Chain Genes

Results from a multiplex RT-PCR of the antibody heavy and light chain genes indicated that a gene product coinciding with the proper molecular size was obtained. Briefly, D1.3 hybridoma cells were lysed using a nonionic detergent (1% NP-40 in 1×PBS) and the lysate was then mixed with rabbit anti-mouse pAb, oligo(dT)-conjugated dual-capture beads for mRNA capture. Generally, a gentle lysis buffer is preferred for cell lysis and can include, in addition to the foregoing: 0.5% NP-40 in 1×PBS or DI water or 0.5% Tween-20 in 1×PBS or DI water. Generally, it is preferable and within the knowledge of those persons skilled in the art to use lysis buffers that can sufficiently lyse the outer membrane of the cell in question, while keeping the nucleus intact. RT-PCR was performed using degenerate primers for both heavy and light chain genes and resulted in bands of the expected size for antibody heavy and light chains (date not shown). The results suggest that dual purpose RNA and antibody beads are capable of capturing RNA suitable for amplification. For comparison, RT-PCR of antibody genes was performed using commercially available oligo(dT) beads and dual-capture beads. The methodology utilized herein is generally as follows:
1) Capture oligo(dT) beads in microfluidic chambers using sieve valves.
2) Load cells in microfluidic chambers.
3) Load antibody-capture beads in chambers.
4) Incubate cells and beads.
5) Measure antibody-antigen binding kinetics.
6) Lyse cells using either a) 1% NP-40 in 1×PBS, or b) alkaline lysis solution (100 mM Tris-HCl, pH 7.5, 500 mM LiCl, 10 mM EDTA, pH 8.0 1% LiDS, 5 mM dithiothreitol (DTT)). During lysis, the cell lysate is flushed over the stack of trapped oligo(dT) beads. The oligo(dT) beads and alkaline lysis solution are from the Dynabead mRNA direct kit developed by Invitrogen, but alternatives to these reagents exist.
7) Wash beads with 1×PBS to remove lysis solution.
8) Open sieve valves.
9) Open microfluidic chamber valves and send beads to an output port (one chamber at a time).
10) Recover beads from output port using a pipette.
11) Pipette beads into 50 microL of one-step RT-PCR mix.
    i) dNTPs;
    ii) mixture of RT and DNA polymerase enzymes;
    iii) degenerate primers for both heavy and light chain genes (PCR reagents from a One-Step RT-PCR kit developed by Qiagen, but could also be prepared ourselves);
12) Perform RT and Touchdown PCR using the following protocol:
    i) RT at 50° C. for 30 min;
    ii) 95° C. for 15 min to inactivate RT enzyme and activate DNA polymerase
    iii) First ten cycles of Touchdown PCR:
       a) 94° C. for 30 s;
       b) 55° C. for 1 min (decrease by 1 C each cycle, until 45 C);
       c) 72° C. for 1 min.
    iv) 30 cycles of PCR
       a) 94° C. for 30 s;
       b) 45° C. for 1 min;
       c) 72° C. for 1 min.
13) Visualize RT-PCR amplicons on 0.5% DNA agarose gel using SYBRsafe fluorescent dye.
14) Extract amplicons from gel and purify using standard gel extraction kit (Qiagen).
15) Sequence samples.

Figure 16A:
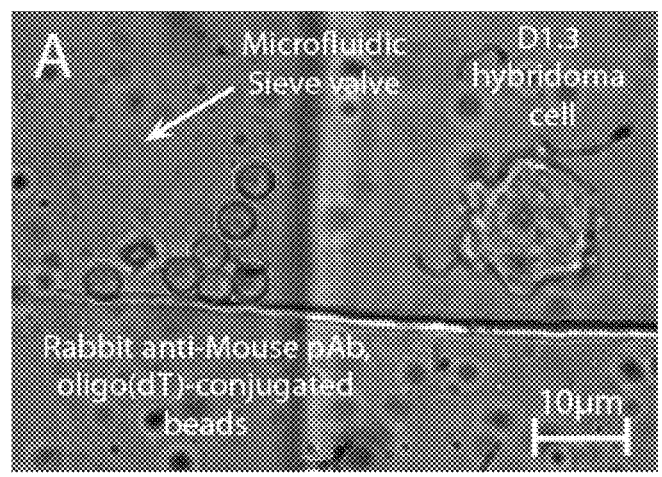
FIGS. 16A-16B show
Figure 16B:
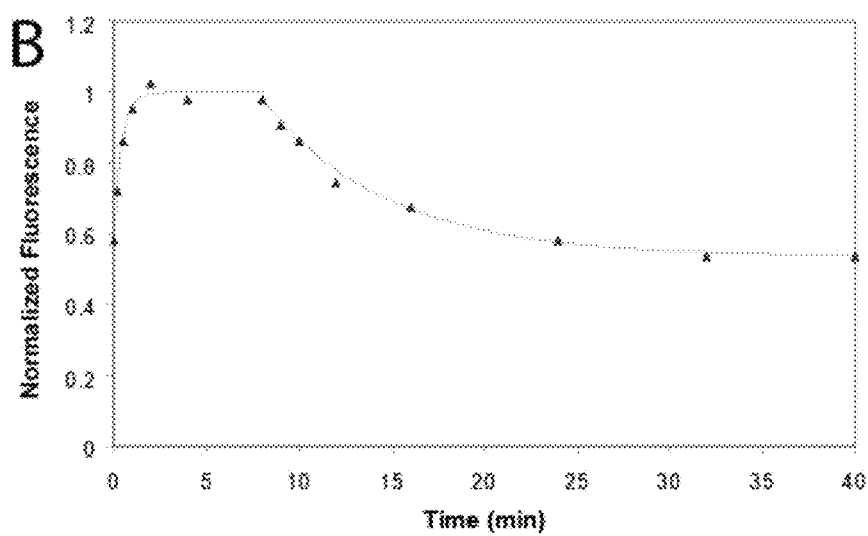

Example 8. Microfluidic Antibody-Antigen Binding Kinetics Measured Using Dual Function Beads and Antibodies Secreted by Single Hybridoma Cells Microscope image of D1.3 hybridoma cell adjacent to Rabbit anti-Mouse pAb, oligo(dT)-conjugated polystyrene beads trapped by a microfluidic sieve valve. After a 2 hour incubation the beads with the D1.3 cell, antibody-antigen binding kinetics were measured using fluorescently labeled HEL-Dylight488 conjugate. These results are highlighted in FIGS. 16A-16B and show that dual purpose beads are suitable for testing antibody-antigen binding kinetics.

Example 9. Mouse Experiment: Antibody Binding Kinetics and Whole-Cell Heavy Chain RT-PCR with Beads These experiments were designed to detect antibodies from primary splenocytes harvested from BALB/c immunized mice. The cells were eluted and whole-cell single-plex RT-PCR was performed of heavy and light chain antibody genes. Thereafter, binding kinetics of the antibodies were measured.

Chip.

Bead v6.6 chip with ~3 micron high sieve channels, 2 micron gratings (fabricated: May 29, 2011 with RTV615).

Reagents.

The following reagents were used herein: 1×PBS for reagent flush; FACS-sorted CD138+ primary splenocytes in RPMI-10-2-ME media; 4.9 micron Rabbit anti-Mouse Protein A beads; 5 microL of stock bead solution resuspended in 100 μL of RPMI-10-2-ME media; and 214 ng/mL HEL488 in 1×PBS.

Experimental Protocol.

The following experimental protocol was followed: washed chip with 1×PBS; closed sieve valves; spun down primary cells and decanted ~400 of 500 μL of media; and re-suspended cells in remaining media.

Thereafter, the cells were loaded in all chambers sequentially with deliberate negative controls included (e.g., R1C14 and R0C02); load 4.9 micron Rabbit anti-Mouse Protein A beads in all chambers sequentially; incubate cells and beads for 1 h 20 min; and wash all chambers with 214 ng/mL HEL488 for 5 min. Thereafter, chamber intensities were analyzed using Image Analysis. Positive chambers were determined as follows: R0C04, R0C08, R2C02, R2C04, R2C07, R2C12, R2C13, R3C06, R4C01, R4C03, R4C05, R5C08, R5C09, R5C12, R5C14, R6C01, R6C02, R6C09, R6C10, R6C11, and R7C05.

RT-PCR mix without primers was prepared from a One-Step RT-PCR kit (Qiagen). The mix comprised: 10 μL 5×RT-PCR buffer×16=160 μL; 21 μL RNase-free water× 16=336 L; 2 μL dNTPs×16=32 μL; 2 μL Enzyme mix× 16=32 μL. The RT-PCR mix without primers was aliquoted into 8 tubes of 70 μL each (2 reaction volumes, not including primer volume).

Prepared primer solutions to be mixed with RT-PCR after cell elution were as follows: Heavy chain—7.5 μL 8 M 3' IgH first primer×8=60 μL; and 7.5 μL 8 M 5' IgH first primer×8=60 μL. Kappa chain—7.5 μL 8 M 3' IgK first primer×8=60 μL; and 7.5 μL 8 M 5' IgK first primer×8=60 μL. 15 μL of primer mixes were aliquoted into each of 8 tubes. The primers used herein were selected based on what is taught in Table II of Tiller et al. (2009) *J. Immunol. Methods* 350: 183-193, which is incorporated herein by reference. Those persons skilled in the art that variants to the primers defined in Table II could be used under certain circumstances including, for example, the primers in Table III in Tiller et al. (2009).

Eight (8) of the brightest chambers [R0C04, R2C04, R2C07, R3C06, R5C12, R5C14, R6C01, R6C10] were eluted. The eluted cell samples were pipetted directly into 70 μL RT-PCR mix without primers. The RT-PCR/cell mix was split into two (2) equal parts of 35 μL and mixed with kappa and heavy chain primers, respectively. RT-PCR was performed using a thermal cycler. Briefly, the "NEST1ST5" protocol was used for the kappa chain reactions, comprising: RT step: 50° C. for 30 min; Hotstart/RT inactivation: 95° C. for 15 min; and 50 Cycles (denaturation: 94° C. for 30 s; anneal: 50° C. for 30 s; and extension: 72° C. for 55 s). Then, there was a final extension: 72° C. for 10 min. Heavy chain reactions performed using the "NEST1H" protocol, comprising: RT step: 50° C. for 30 min; Hotstart/RT inactivation: 95° C. for 15 min; and 50 Cycles (denaturation: 94° C. for 30 s; anneal: 56° C. for 30 s; extension: 72° C. for 55 s). Then, there was a final extension: 72° C. for 10 min.

Figure 17A:
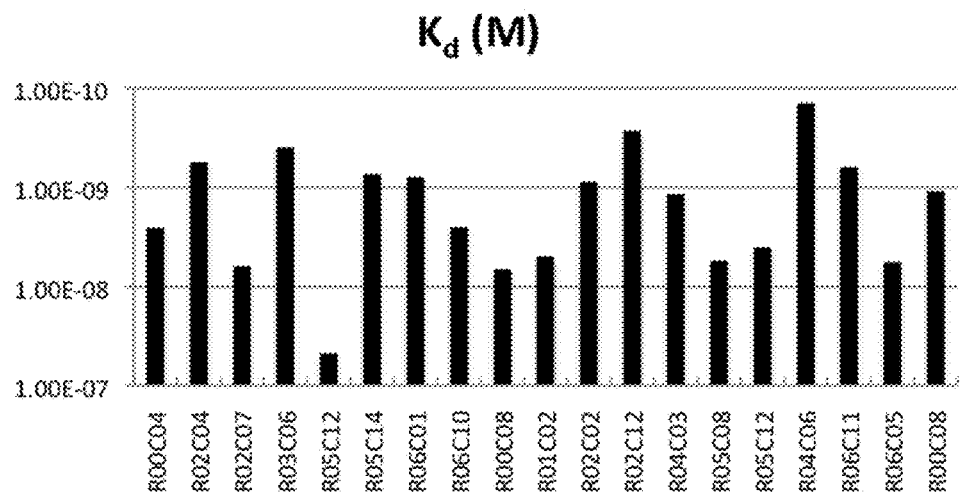
FIGS. 17A-17C depicts
Figure 17B:
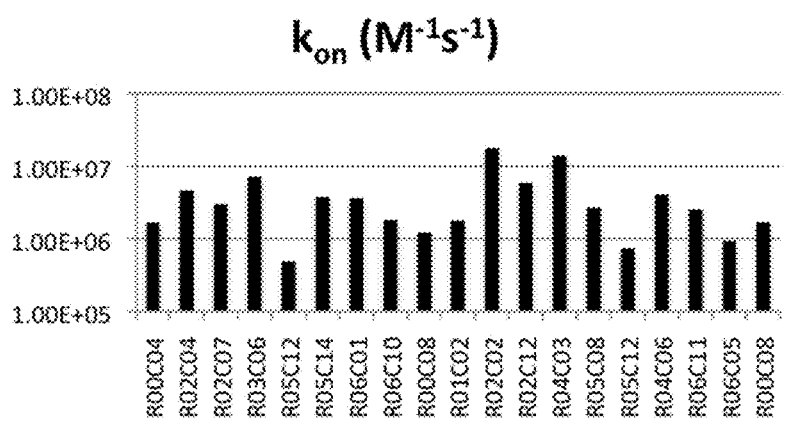
Figure 17C:
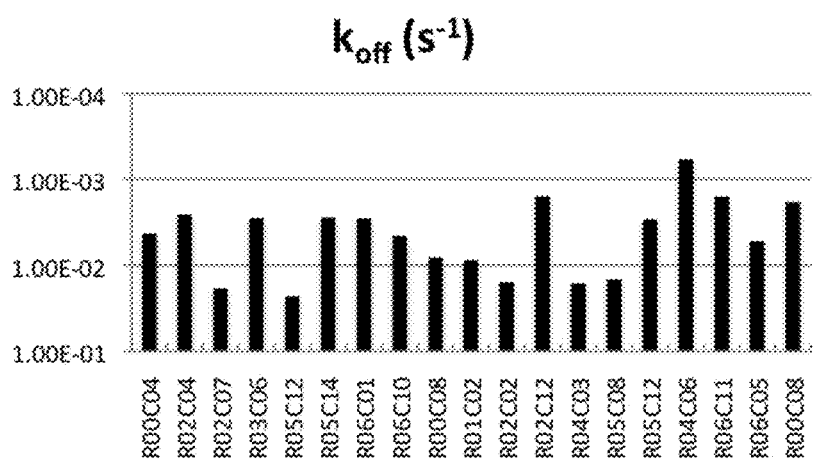
Figure 18A:
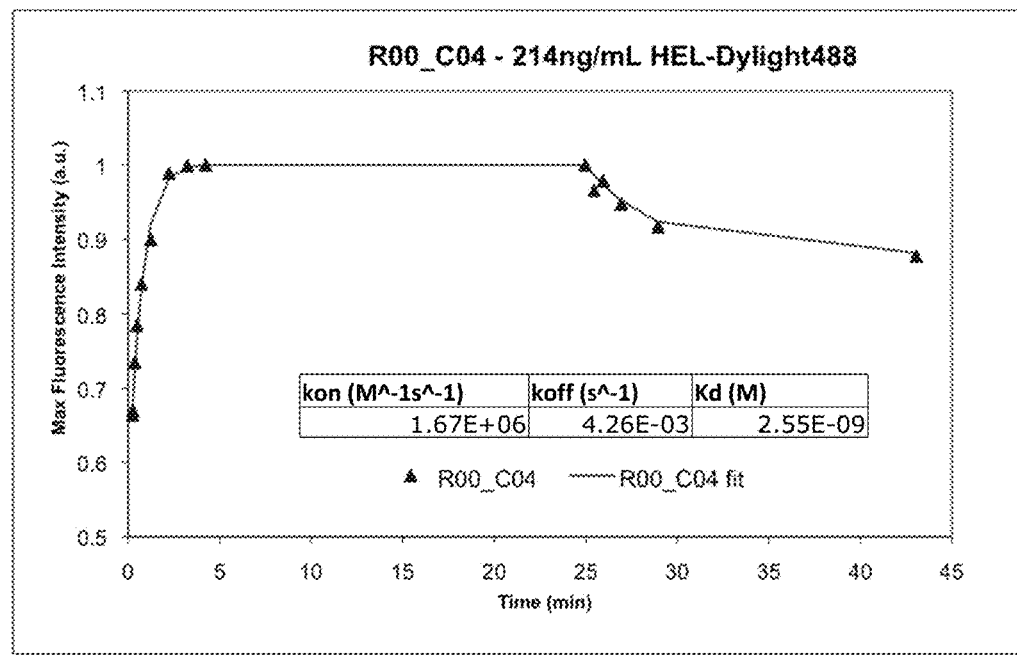
FIGS. 18A-18B show representative fluorescence intensity data over time for specific eluted chambers according to Example 9 herein.
Figure 18B:
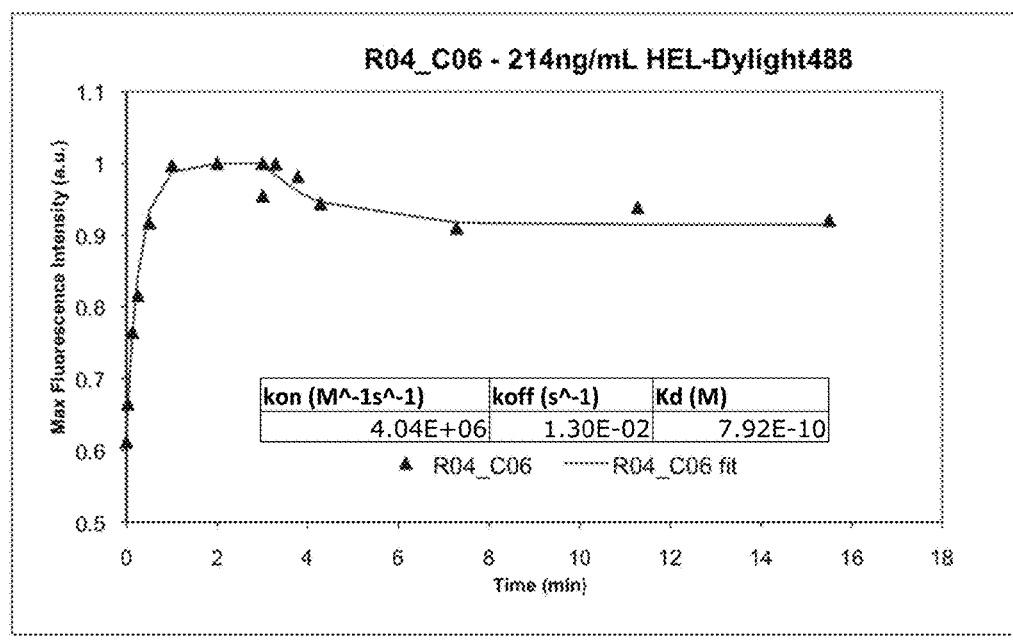

Thereafter, kinetics were measured on each of the eluted chambers. A summary of the kinetics data is shown in FIGS. 17A-17C. Representative kinetics sample data is shown in each of FIGS. 18A-18B herein. Dissociation kinetics were measured and then association kinetics were measured using freshly loaded HEL488. Thereafter, a second round of single-plex RT-PCR was performed using nested second round primers. The heavy chain mix comprised of: 10 μL 5×RT-PCR buffer×8=80 μL; 21 μL RNase-free water×8=168 μL; 2 μL dNTPs×8=16 μL; 2 μL Enzyme mix×8=16 μL; 7.5 μL 8 μM 3' IgH second primer×8=45 μL; and 7.5 μL 8 M 5' IgH second primer×8=45 μL. The kappa chain mix comprised of: 10 μL 5×RT-PCR buffer×8=80 μL; 21 μL RNase-free water×8=168 μL; 2 μL dNTPs×8=16 μL; 2 μL Enzyme mix×8=16 μL; 7.5 μL 8 M 3' IgK second primer×8=45 μL; and 7.5 μL 8 μM 5' IgK second primer×8=45 μL. Thereafter, 3.5 μL of template from each of the first round reactions was added and RT-PCR was performed on a thermal cycler. Kappa chain reactions were performed using the "NEST2K" protocol. Briefly, there was no RT step; hotstart/RT inactivation was at 95° C. for 15 min followed by 50 cycles (denaturation: 94° C. for 30 s; anneal: 45° C. for 30 s; and extension: 72° C. for 55 s). Then, there was a final extension: 72° C. for 10 min.

Figure 19A:
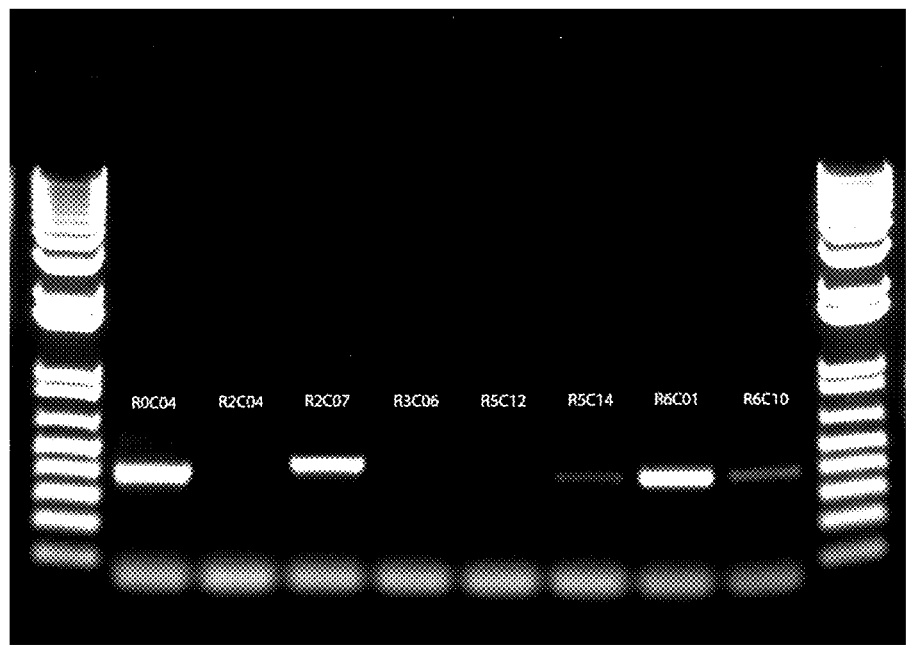
FIGS. 19A-19D show Kappa chain results from the first round of RT-PCR are shown in FIG. 19A. Kappa chain results from the second round of RT-PCR are shown in FIG. 19B. Heavy chain results from the first round of RT-PCR are shown in FIG. 19C. Heavy chain results from the second round of RT-PCR are shown in FIG. 19D.
Figure 19B:
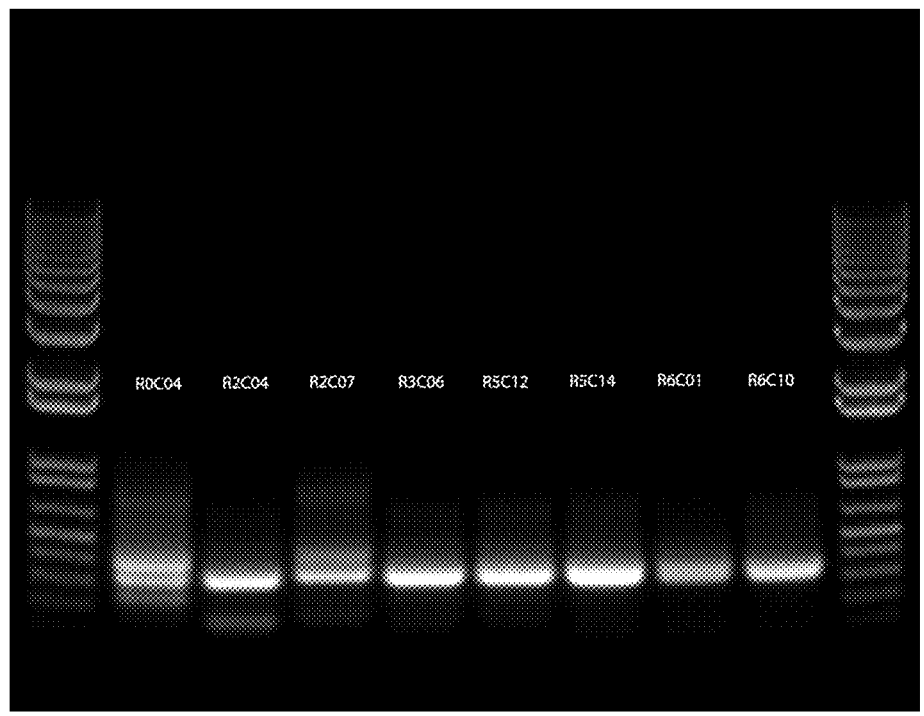
Figure 19C:
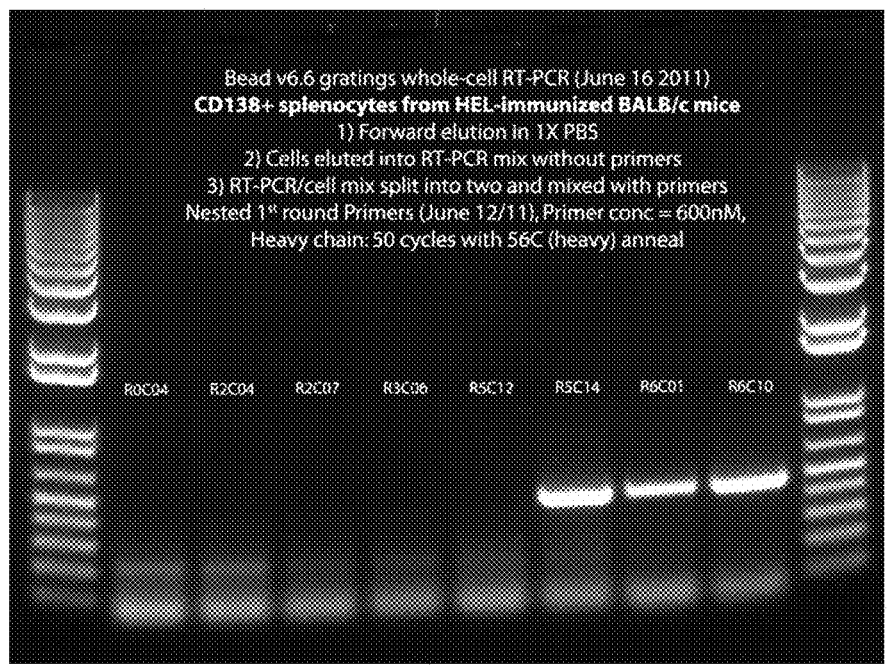
Figure 19D:
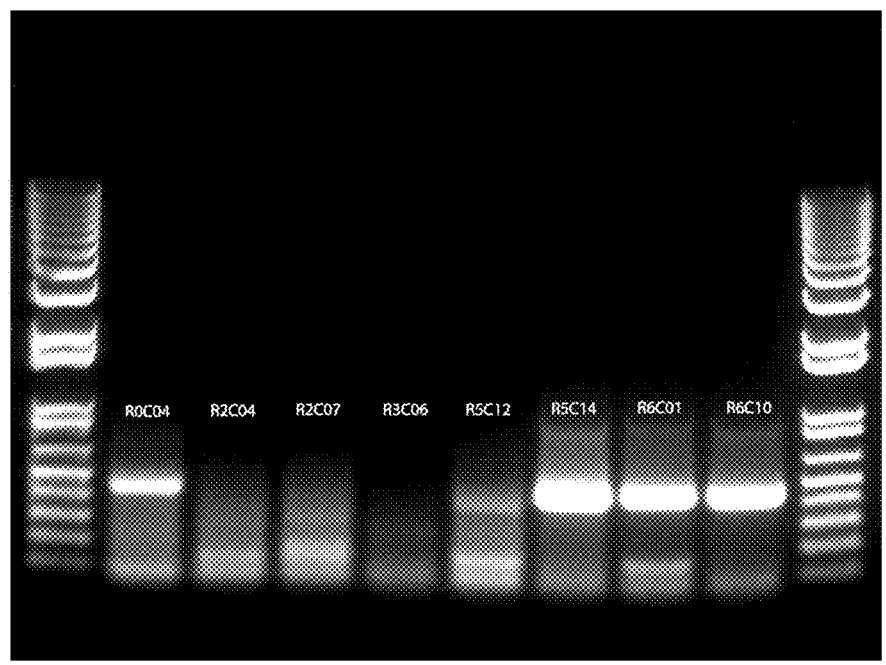

Heavy chain reactions performed using the "NEST2H" protocol. Briefly, there was no RT step; hotstart/RT inactivation: 95° C. for 15 min, followed by 50 cycles (denaturation: 94° C. for 30 s; anneal: 60° C. for 30 s; and extension: 72° C. for 55 s). Then, there was a final extension: 72° C. for 10 min. The RT-PCR products for both first and second round reactions were run on a gel. Kappa chain results from the first round are shown in FIG. 19A. Kappa chain results from the second round are shown in FIG. 19B. Heavy chain results from the first round are shown in FIG. 19C. Heavy chain results from the second round are shown in FIG. 19D. The gel products were sequenced by standard procedures known to those skilled in the art. Based on the sequence data generated, variants in antibody sequences were detectable. As a representative example, mutations in the R00C04 sample are shown in Table 2 herein.

TABLE 2

| R00C04 (9 non-synonymous mutations) | | | |
|---|---|---|---|
| Position (from IMGT) | Situation (from IMGT) | Germline Ab residue | R00C04 Ab residue |
| L-36 | CDR1-L | S | N |
| L-92 | FR3-L | S | T |
| H-17 | FR1-H | A | D |
| H-36 | CDR1-H | S | R |
| H-40 | FR2-H | H | L |
| H-64 | CDR2-H | N | K |
| H-65 | CDR2-H | T | S |
| H-83 | FR3-H | S | I |
| H-94 | FR3-H | P | L |

Example 10. Microfluidic Device

Figure 20A:
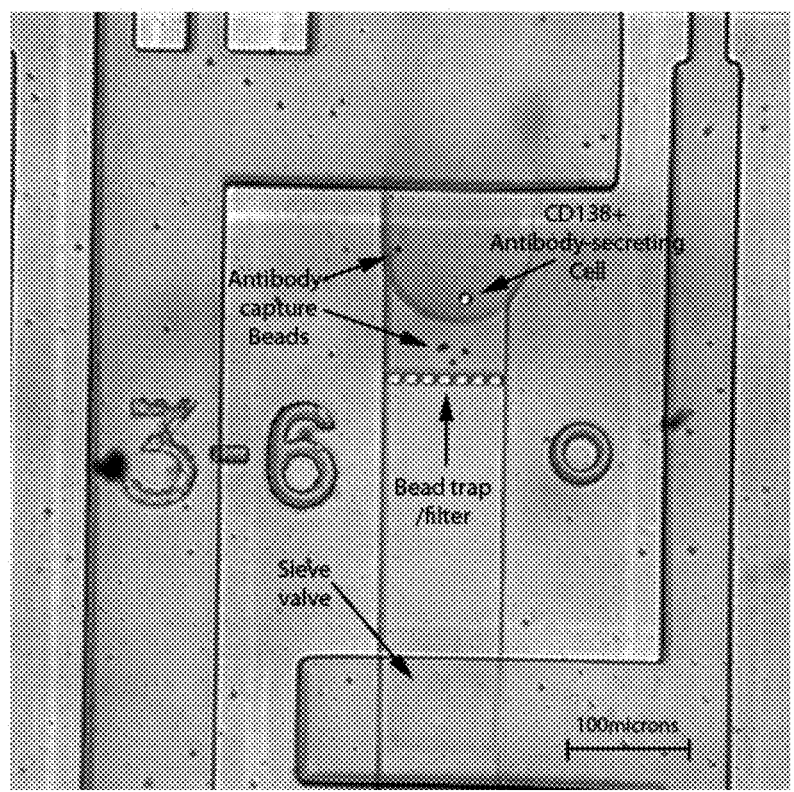
FIGS. 20A-20B show a microfluidic device according to an embodiment of the invention described herein, showing a reversible trap.
Figure 20B:
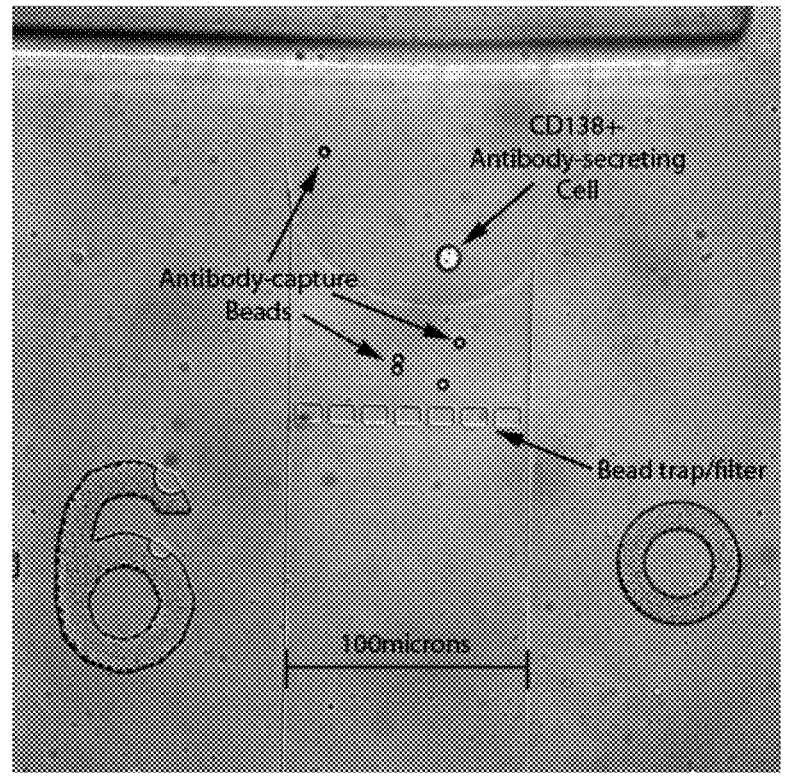
Figure 21A:
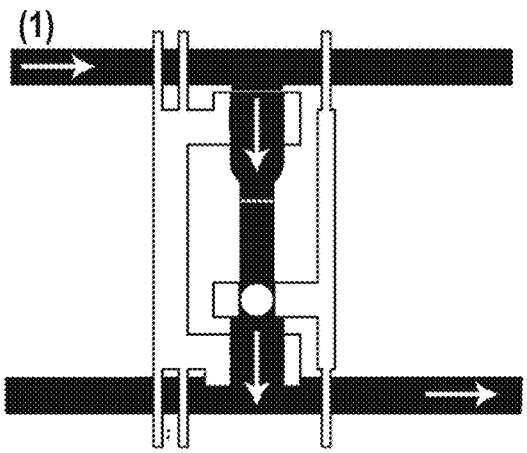
FIGS. 21A-21J show a schematic whereby a microfluidic device according to an embodiment of the invention described herein is used as described herein.
Figure 21B:
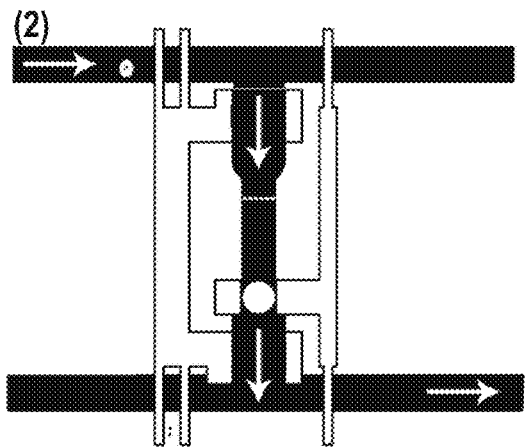
Figure 21C:
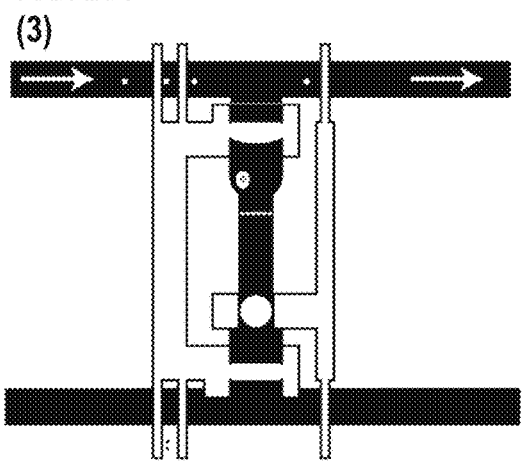
Figure 21D:
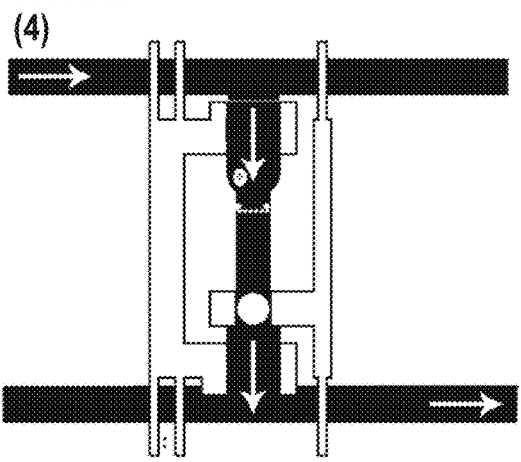
Figure 21E:
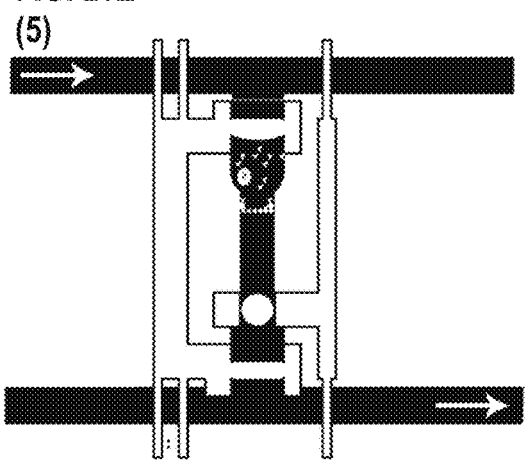
Figure 21F:
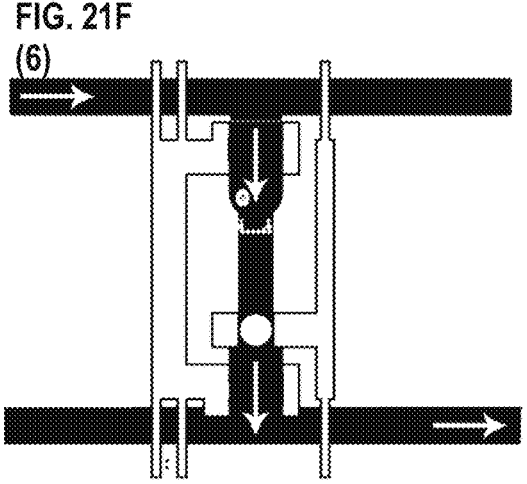
Figure 21G:
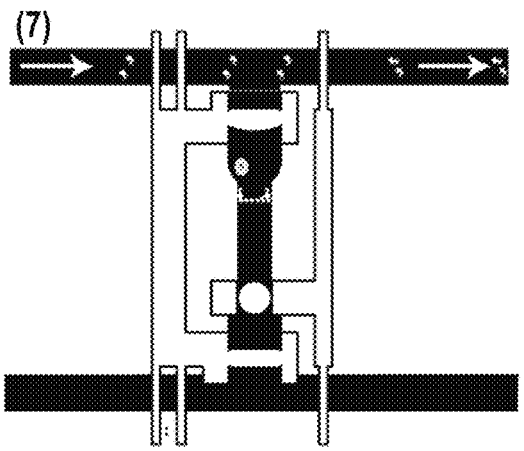
Figure 21H:
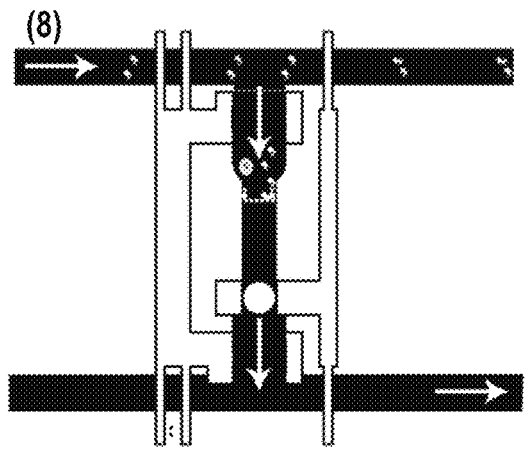
Figure 21I:
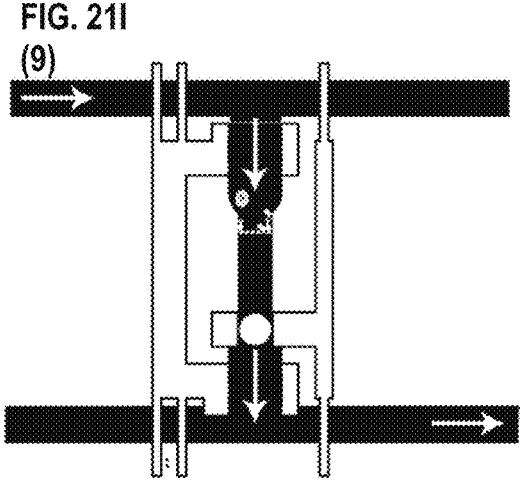
Figure 21J:
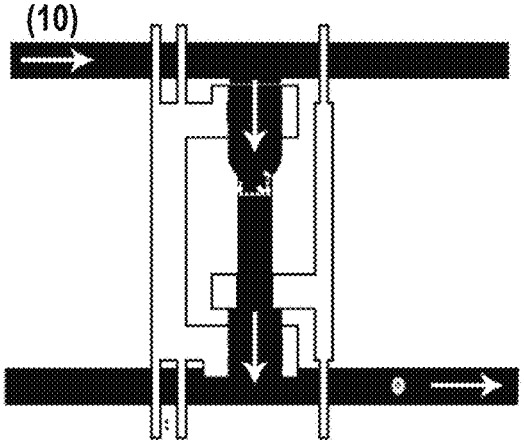
Figure 22:
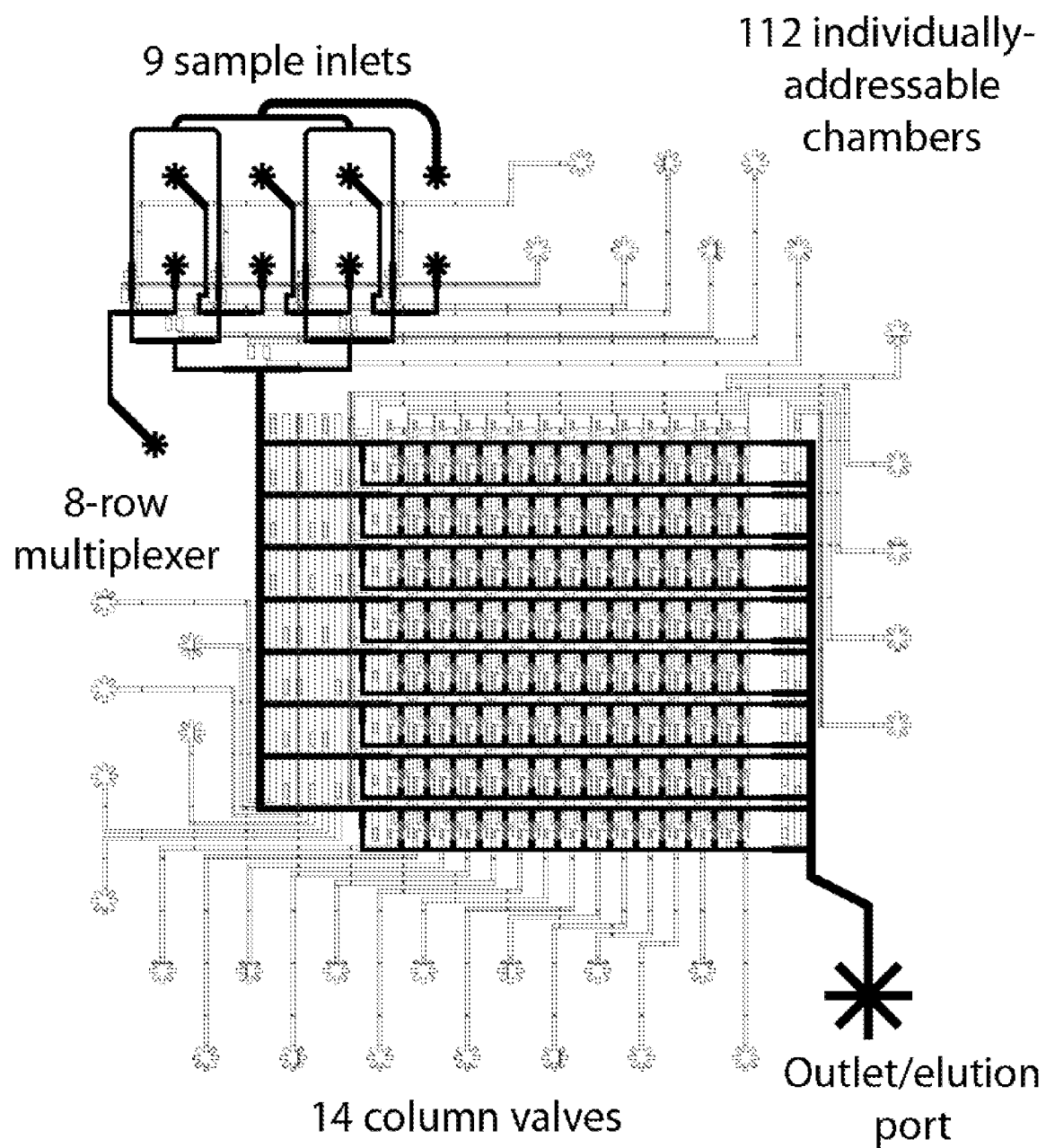
FIG. 22 shows a schematic diagram of an alternative embodiment of the microfluidic device for assaying binding interactions.

A microfluidic device has been developed for assaying a binding interaction between a protein produced by a cell and a biomolecule. The device has a chamber having an aperture and a channel for receiving a flowed fluid volume through the chamber via said aperture. The channel provides for size selection for a particle within the fluid volume. Alternately, another embodiment of the microfluidic device has a chamber having an aperture and a reversible trap. The reversible trap has spaced apart structural members extending across the chamber. The structural members are operable to allow a fluid volume to flow through the chamber while providing size selection for a particle within the fluid volume. See, for example: FIGS. 20A-20B herein.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. The invention includes all embodiments and variations substantially as hereinbefore described and with reference to the examples and drawings. Further, citation of references herein is not an admission that such references are prior art to the present invention nor does it constitute any admission as to the contents or date of these documents.

What is claimed is:

1. A method of assaying for a binding interaction between a secreted monoclonal antibody produced by a single antibody producing cell (APC) and an antigen, the method comprising:
   retaining the single APC within a chamber having a volume of from 100 pL to 100 nL, a solid wall, and an aperture that defines an opening of the chamber;
   incubating the single APC within the chamber to produce a secreted monoclonal antibody;
   exposing the secreted monoclonal antibody to a first removeable capture substrate bound to an antigen, wherein the antigen is capable of capturing the secreted monoclonal antibody,
   incubating the secreted monoclonal antibody with the first removeable capture substrate to produce a bound antibody; and
   measuring a binding interaction between the bound antibody and the antigen.

2. The method of claim 1, wherein the single APC is a primary B cell or a memory B cell.

3. The method of claim 1, wherein the single APC is a primary plasma cell.

4. The method of claim 1, wherein the single APC is from a human, a rabbit, a rat, a mouse, a sheep, an ape, a monkey, a goat, a dog, a cat, a camel, or a pig.

5. The method of claim 1, wherein the antigen is fluorescently labeled.

6. The method of claim 5, further comprising lysing the single APC to provide a lysed APC.

7. The method of claim 6, further comprising capturing the nucleic acids of the lysed APC on a second removeable capture substrate.

8. The method of claim 7, wherein the second removeable capture substrate comprises an oligo(dT) mRNA capture bead capable of binding mRNA.

9. The method of claim 7, wherein the second removeable capture substrate is capable of binding nucleic acids encoding the variable regions of the secreted monoclonal antibody and capturing the nucleic acids comprises capturing nucleic acids encoding the variable regions of the secreted monoclonal antibody.

10. The method of claim 8, further comprising washing the second removeable capture substrate after lysing.

11. The method of claim 9, further comprising washing the second removeable capture substrate after lysing.

12. The method of claim 1, further comprising recovering the first removeable capture substrate.

13. The method of claim 7, further comprising recovering the second removeable capture substrate.

14. The method of claim 8, further comprising recovering the second removeable capture substrate.

15. The method of claim 9, further comprising recovering the second removeable capture substrate.

16. The method of claim 1, wherein measuring the binding interaction comprises measuring an antigen-antibody binding kinetic property between the antigen and the bound antibody.

17. The method of claim 16, wherein the antigen-antibody binding kinetic property is a $K_{on}$ rate; a $K_{off}$ rate, a dissociation constant, or a combination thereof.

18. The method of claim 1, wherein measuring the binding interaction comprises measuring the affinity of the bound antibody and the antigen.

19. The method of claim 1, wherein measuring the binding interaction comprises measuring the avidity of the bound antibody and the antigen.

20. The method of claim 1, wherein the antigen is a cell fragment, a bacterium, a virus, a viral fragment, or a protein.

21. The method of claim 1, wherein the aperture serves as the inlet and the outlet of the chamber.

22. The method of claim 1, wherein measuring the binding interaction comprises fluorescence imaging of the secreted monoclonal antibody binding to the antigen.

23. The method of claim 1, wherein measuring the binding interaction is carried out via surface plasmon resonance (SPR) spectroscopy, fluorescence anisotropy, interferometry or fluorescence resonance energy transfer (FRET).

24. The method of claim 1, further comprising performing a reverse transcription polymerase chain reaction (RT-PCR) on the nucleic acids of the single APC to amplify the heavy and light chain genes of the secreted monoclonal antibody.

25. The method of claim 6, further comprising performing a reverse transcription polymerase chain reaction (RT-PCR) on the nucleic acids of the APC to amplify the heavy and light chain genes of the secreted monoclonal antibody.

26. The method of claim 7, further comprising performing a reverse transcription polymerase chain reaction (RT-PCR) on the nucleic acids of the APC to amplify the heavy and light chain genes of the secreted monoclonal antibody.

27. The method of claim 13, further comprising performing a reverse transcription polymerase chain reaction (RT-PCR) on the nucleic acids of the APC to amplify the heavy and light chain genes of the secreted monoclonal antibody.

28. The method of claim 25, further comprising sequencing the nucleic acids encoding the variable regions of the secreted monoclonal antibody.

29. The method of claim 26, further comprising sequencing the nucleic acids encoding the variable regions of the secreted monoclonal antibody.

30. The method of claim 27, further comprising sequencing the nucleic acids encoding the variable regions of the secreted monoclonal antibody.

* * * * *